US009399779B2

(12) United States Patent
Daines et al.

(10) Patent No.: US 9,399,779 B2
(45) Date of Patent: Jul. 26, 2016

(54) ALTERNATIVE SPLICING CONSTRUCTS AND METHODS OF USE

(75) Inventors: Dayle A. Daines, Macon, GA (US); Robert J. McKallip, Forsyth, GA (US)

(73) Assignee: The Corporation of Mercer University, Macon, GA (US)

(*) Notice: Subject to any disclaimer, the term of this patent is extended or adjusted under 35 U.S.C. 154(b) by 233 days.

(21) Appl. No.: 13/485,146

(22) Filed: May 31, 2012

(65) Prior Publication Data
US 2012/0315643 A1 Dec. 13, 2012

Related U.S. Application Data

(60) Provisional application No. 61/494,529, filed on Jun. 8, 2011.

(51) Int. Cl.
| C12Q 1/68 | (2006.01) |
| C12N 15/85 | (2006.01) |
| C07K 14/705 | (2006.01) |
| C07H 21/02 | (2006.01) |
| C07H 21/04 | (2006.01) |
| C12N 15/09 | (2006.01) |
| C12N 15/12 | (2006.01) |
| C12N 15/63 | (2006.01) |
| C12N 15/65 | (2006.01) |

(52) U.S. Cl.
CPC .......... *C12N 15/85* (2013.01); *C07K 14/70585* (2013.01); *C12N 2840/44* (2013.01)

(58) Field of Classification Search
None
See application file for complete search history.

(56) References Cited

U.S. PATENT DOCUMENTS

| 2008/0171042 A1* | 7/2008 | Iczkowski ............ C12N 15/113 424/138.1 |
| 2010/0035983 A1* | 2/2010 | Shiffman .............. C12Q 1/6883 514/510 |
| 2010/0120022 A1* | 5/2010 | Ayalon-Soffer et al. .......... 435/6 |
| 2010/0215656 A1* | 8/2010 | Pastan et al. ............... 424/134.1 |

FOREIGN PATENT DOCUMENTS

| WO | WO2009007934 | * | 1/2009 |
| WO | WO2011022335 | * | 2/2011 |

OTHER PUBLICATIONS

Hayes et al. Cancer Gene Therapy (2004) 11, 797-807.*
Screaton et al. Proc Natl Acad Sci U S A. Dec. 15, 1992;89(24):12160-4.*
Lamb et al. Mol. Cell. Biol. Feb. 1997 vol. 17 No. 2 963-976.*
Afify, A., McNiel, M.A., et al. (2008) Expression of CD44s, CD44v6, and hyaluronan across the spectrum of normal-hyperplasia-carcinoma in breast. Appl Immunohistochem Mol Morphol 16(2): 121-127.
Bemmo, A., Dias, C., et al. (2010) Exon-level transcriptome profiling in murine breast cancer reveals splicing changes specific to tumors with different metastatic abilities. PloS ONE 5(8): 1-13.
Brinkman, B. M. N. (2004) Splice variants as cancer biomarkers. Clinincal Biochemistry 37: 584-594.
Charpin, C., Guisiano, S., et al. (2009) Quantitative immunocytochemical profile to predict early outcome of disease in triple-negative breast carcinomas. International Journal of Oncology 34: 983-993.
Fox, S. B., Fawcett, J., et al. (1994) Normal human tissues, in addition to some tumors, express multiple different CD44 isoforms. Cancer Research 54:4539-4546.
Gruber, C., Gratz, I. K., et al. (2011) Spliceosome-mediated RNA trans-splicing facilitates targeted delivery of suicide genes to cancer cells. Mol. Cancer Ther. 10: 233-241.
Hayes, G. M., Carpenito, C., et al. (2002) Alternative splicing as a means of regulating the expression of therapeutic genes. Cancer Gene Therapy 9: 133-141.
Heider, K.-H., Kuthan, H., et al. (2004) CD44v6: a target for antibody based cancer therapy. Cancer Immunol. Immunother. 53: 567-579.
Hong, S. C., Song, J. Y., et al. (2006) Significance of CD44v6 expression in gynecologic malignancies. J. Obstet. Gynaecol. Res. 32(4): 379-386.
Iczkowski, K. A., Bai, S., & Pantazis, C. G. (2003) Prostate cancer overexpresses CD44 variants 7-9 at the messenger RNA and protein level. Anticancer Research 23: 3129-3140.
Iglewski, B. H. & Kabat, D. (1975) NAD-dependent inhibition of protein synthesis by Pseudomonas aeruginosa toxin. Proc. Nat. Acad. Sci. USA 72(4): 2284-2288.
Iglewski, B. H., Liu, P. V., & Kabat, D. (1977) Mechanism of action of Pseudomonas aeruginosa exotoxin A: adenosine diphosphate-ribosylation of mammalian elongation factor 2 in vitro and in vivo. Infection and Immunity 15 (1): 138-144.
Messina, M., Yu, D. M. T., et al. (2003) Calcitonin-specific transcription and splicing targets gene-directed enzyme prodrug therapy to medullary thyroid carcinoma cells. Journal of Clinical Endocrinology & Metabolism 88(3): 1310-1318.
Mosmann, T. (1983) Rapid colorimetric assay for cellular growth and survival: aplication to proliferation and cytotoxicity assays. Journal of Immunological Methods 65:55-63.
Navaglia, F., Fogar, P., et al. (2003) CD44v10: an antimetastatic membrane glycoprotein for pancreatic cancer. International Journal of Biological Markers 18(2): 130-138.
Negoescu, A., Guillermet, C., et al. (1998) Importance of DNA fragmentation in apoptosis with regard to TUNEL specificity. Biomed. & Pharmacother. 52(6): 252-258.
Ogawa, R., Kagiyama, G., et al. (2007) Construction of strong mammalian promoter by random cis-acting element elongation. BioTechniques 42: 628-633.
Rupp, U., Schoendorf-Holland, E., et al. (2007) Safety and pharmacokinetics of bivatuzumab mertansine in patients with CD44v6-positive metastatic breast cancer: final results of a phase I study. Anti-Cancer Drugs 18: 477-485.

(Continued)

*Primary Examiner* — Nancy J Leith
(74) *Attorney, Agent, or Firm* — Withers & Keys, LLC

(57) ABSTRACT

Provided are alternative splicing constructs and methods for their use. In particular, CD44 based alternative splicing constructs are provided that include CD44 exon 5. These alternative splicing constructs are useful in high-throughput assays for testing the effects of compounds on splicing and for achieving targeted cell death.

22 Claims, 14 Drawing Sheets

(56) References Cited

OTHER PUBLICATIONS

Schmitt, C.K., Meysick, K.C., & O'Brien, A.D. (1999) Bacterial toxins: friends or foes? Emerging Infectious Diseases 5(2): 224-234.

Schimada, M. K., Hayakawa, Y., et al. (2010) A comprehensive survey of human polymorphisms at conserved splice dinucleotides and its evolutionary relationship with alternative splicing. BMC Evolutionary Biology 10:122.

Snyder, E. L., Bailey, D., et al. (2009) Identification of CD44v6+/CD24− breast carcinoma cells in primary human tumors by quantum dot-conjugated antibodies. Laboratory Investigation 89: 857-866.

Stroomer, J. W. G., Roos, J. C., et al. (2000) Safety and biodistribution of 99mTechnetium-labeled anti-CD44v6 monoclonal antibody BIWA 1 in head and neck cancer patients. Clinical Cancer Research 6: 3046-3055.

Vela, E., Hilari, J. M., et al. (2007) Multisite and bidirectional exonic splicing enhancer in CD44 alternative exon v3. RNA 13: 2312-2323.

Wachtel, C. & Manley, J. L. (2009) Splicing of mRNA precursors: the role of RNAs and proteins in catalysis. Molecular BioSystems 5: 311-316.

Weldon, J. E. & Pastan, I. (2011) A guide to taming a toxin—recombinant immunotoxins constructed from Pseudomonas exotoxin A for the treatment of cancer. FEBS Journal 278: 4683-4700.

* cited by examiner

A. General Alternative Splicing Construct
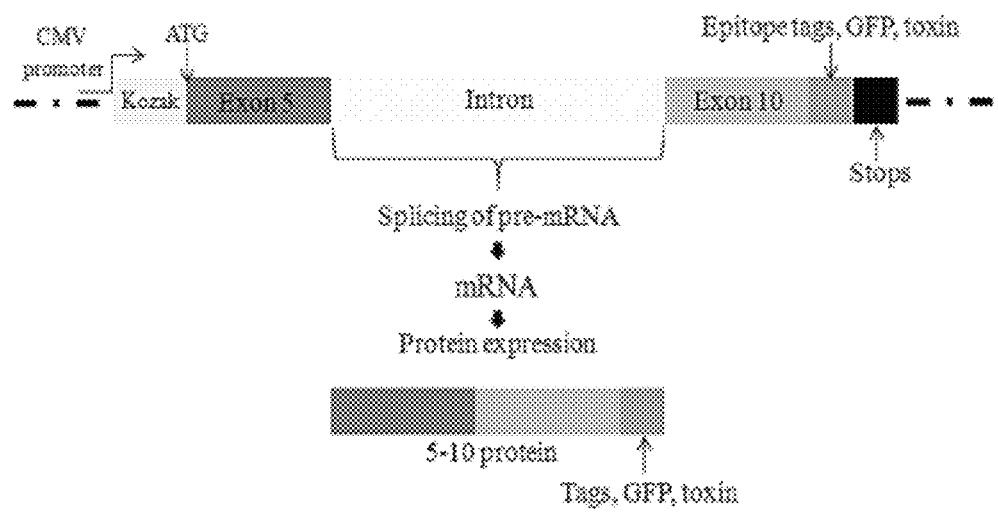
B. RT-PCR of test plasmid pDD826
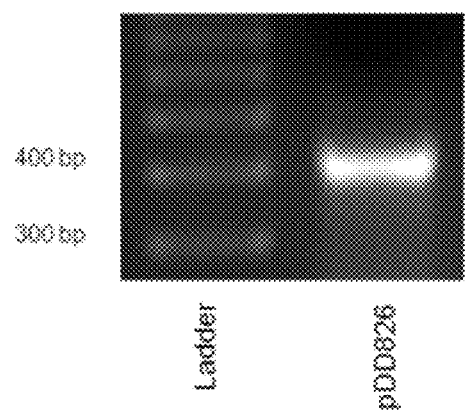
FIG. 2

SEQ ID NO:8

GTACATCAGTCACAGACCTGCCCAATGCCTTTGATGGACCAAT
TACCATAA*CTATTGTTAACCGTGATGGCACCCGCTATGTCCAG*
*AAAGGAGAATACAGAACGAATCCTGAAGACATCTACCCCAGCA*
*ACCCTACTGATGATGACGTGAGCAGCGGCTCCTCCAGTGAAAG*
*GAGCAGCACTTCAGGAGGTTACATCTTTTACACCTTTTCTACT*
*GTACACCCCATCCCAGACGAAGACAGTCCCTGGATCACCGACA*
*GCACAGACAGAATCCCTGCTACCA*ATATGGACTCCAGTCATAG
TATAACGCTTCAGCCTACTGCAAATCCAAACACAGGTTTGGTG
GAAGATTTGGACAGGACAGGACCTCTTTCAATGACAACGCAGC
AGAGTAATTCTCAGAGCTTCTCTACATCA

Italics = Exon 5
Underlined = Exon 12

FIG. 11B

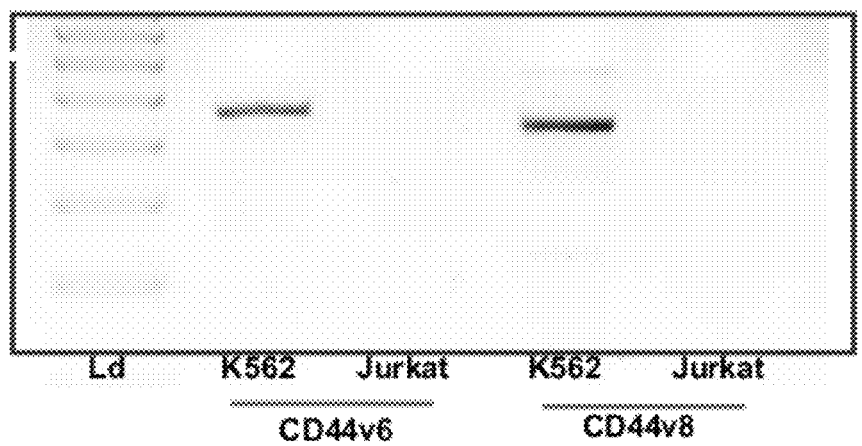

FIG. 12A

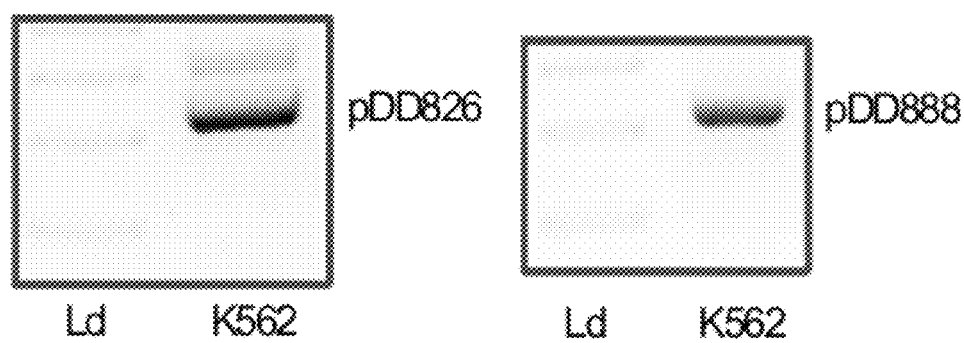

FIG. 12B

Brightfield
Fluorescence
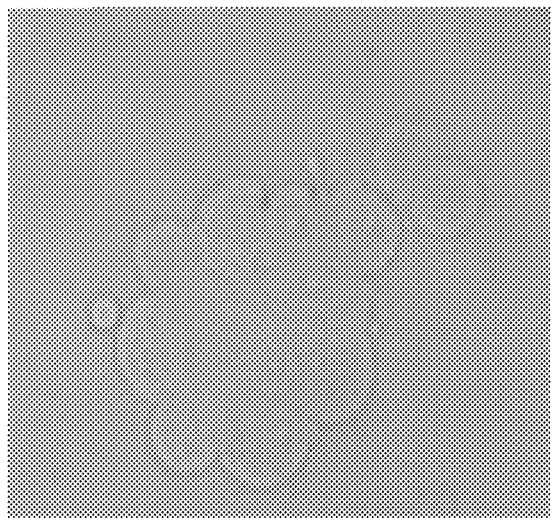
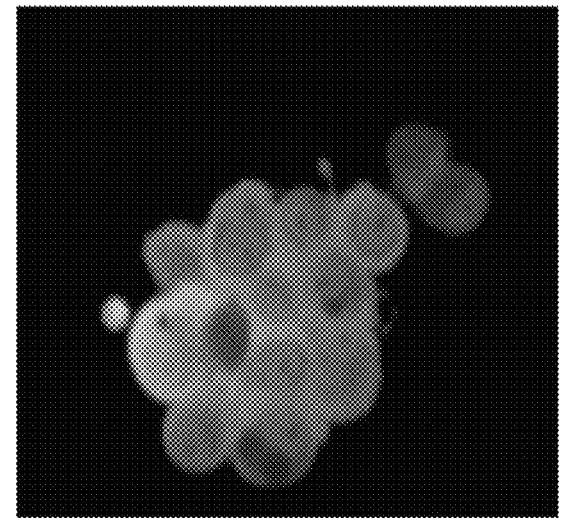
FIG. 16C
FIG. 16D
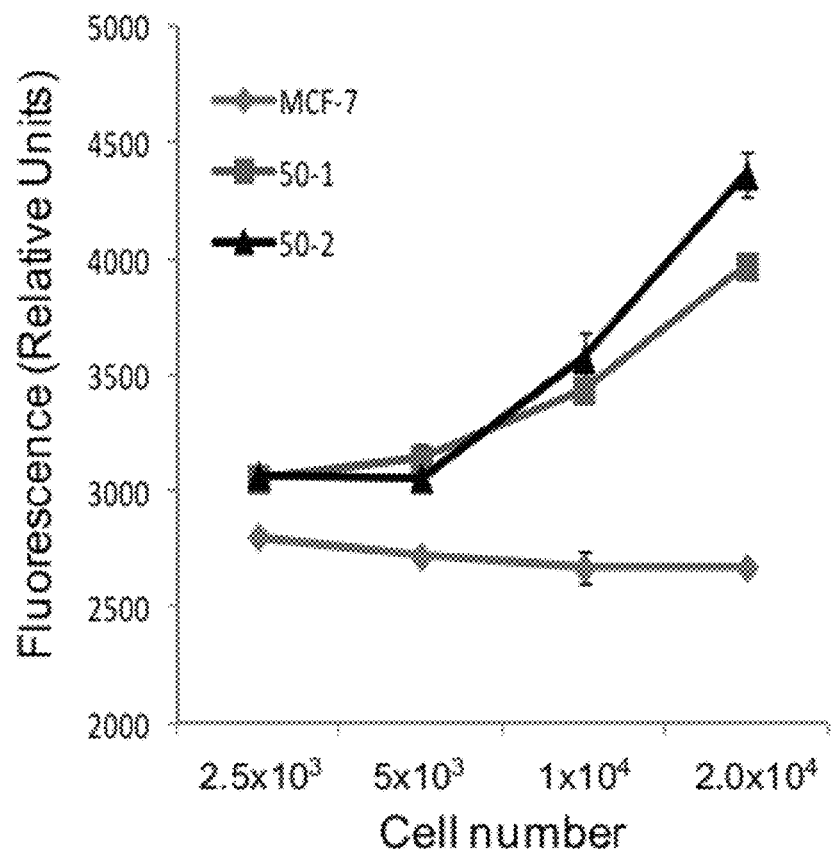
FIG. 17

SEQUENCE LISTING

```
<160> NUMBER OF SEQ ID NOS: 8

<210> SEQ ID NO 1
<211> LENGTH: 231
<212> TYPE: DNA
<213> ORGANISM: Homo sapiens

<400> SEQUENCE: 1
ctattgttaa ccgtgatggc acccgctatg tccagaaagg agaatacaga acgaatcctg      60
aagacatcta ccccagcaac cctactgatg atgacgtgag cagcggctcc tccagtgaaa     120
ggagcagcac ttcaggaggt tacatctttt acaccttttc tactgtacac cccatcccag     180
acgaagacag tccctggatc accgacagca cagacagaat ccctgctacc a              231

<210> SEQ ID NO 2
<211> LENGTH: 2724
<212> TYPE: DNA
<213> ORGANISM: Homo sapiens

<400> SEQUENCE: 2
gtaagcaaga tggcggtcgg cagttctggg ttagatgaat tagtaaagac attccagcaa      60
tagggaagat tttgtttaga aattggccgc atcttctatt tccactcggt aatttctttt     120
attcttagag cctgaaaagc tgctaaaccc gcacacaaat tttaaaaatt ggaaggaaaa     180
tgataactca tcaggttgcc caaaggccaa aatgttttaa gaagtagatc tagatacaat     240
ttttgtgtta aaggttccta gaggttccat ttgggtaact tgtgtgtgtt cattgaaatg     300
tgtggcaaag agtgtgttct tttggtgctt agtagtggaa tctggaaaga aagtttgtca     360
agtgaattga tctttggaat ccttatttc tatgaagatc tttgatgaat acagtgtctt      420
ttttgcattc tgtccctgac tgttctatag aaagacatcc cttgtactct ttagagcaaa     480
gttggtagct cttatggtct tcatttgaat tctaccactg cttctttttc tgtttttaag     540
cccatggtaa cttggggaag gctttgatgc tcttactgtt atttctacta ttatgaaaac     600
tcaggttttc caaaacaatc tcaagttgcg gcagtggact gtgagaatag ggggcccct      660
```

```
cactcccaa acataagaag tatgtgcttt tcttcttta tctatcccgc tgagatatgt      720
ctatcttatt tggaataaaa gtatttattt tggaaaacag ctttttagca tttttaaaat    780
gatgacccaa ctgtcattct cacagcccta gatacaccta atggggaaat gtgagccact    840
taaaagccac ttaaaaacca aagggctttg ggaatctatg gcttgagggg tgccttcaga    900
taacaaaaga aaagtttcag gtatcagtta ggatagaggt tagacattgt actgaatata    960
tccagcagat cttacatccc attacaaacc ccagtaggtg tgttgtatac atacggctta    1020
ggggttaagt taacaaagaa gtctgataag aaaaggaaat acagaggaag cataaatctc    1080
tttggaatag gattttgttc cactcccctta gagccctaac agtataccctt agaaattatt   1140 ttagacagtt tgtacttaaa gaccagaaag ctactttaga gacttggaaa taatgagcct    1200
attgtcaaaa ggtggtgctt gcggggcatt aggactagag ggttggtgaa aattcagaca    1260
gaatgtaact tgacaaagag aagacagcaa caactgtaac aattatctta tgaatatttg    1320
cgaaactcaa agggatctga ttggtgacct ctgggcttta tcaaattaac atcacaactt    1380
ctagaagaaa gtcaaccttc atcttttaca atagaaatca tatgtttgc taacccattc     1440 ctatttaggc tgaaaacaat taagagttat gggtacttaa aaaaatcatt atgtttataa    1500
aattagtgat agaaggagca tagtgttcta tacagtcaca cacatacact tccttatttc    1560 tttatttaa actttgagta acatagcagt ctatgtttgg gtcagttttc cctttttgt      1620 aattacattc agtggttttt gtaacttcat tatttattgg gaattagtga tttagtcagt    1680
gggagttttg taaaacttaa gattttggct ttttccccc tcctcctgga taaccagtta     1740
acccaataat ggcttggccg atggaagggt aaaatgagga cagttatatt ttttaaatgt    1800
cattactgtc accaaatcac acatatcatt ttctaagata aggaaataca accattttta    1860
caagttgcaa aaaagtactc tggcttggca agtttataga ctctcatttt cttgataaac    1920
taaaaaaaaa aaagaaattg ctacaagctg ctatagacaa aaatgttggt gtctttctga    1980
cttttcctga agacaccttg atggaattat attctcttga ttttgtcctt tttaaaatga    2040
tggttgaaat tttaagcctg tcacacacta ttatttatat aatgcctcaa actggcttgg    2100
atagttttcg tcaactgaat taattttgtt aaaaagtgat tttagcaatt ttaggtgcca    2160
tgtggacatc accaaatact gtgttagtgg aatagcatcc aagccatccc accatctttc    2220
ctgctgggca aatccactgc tggtgcattt ccagtgtgtg cgattatggg ttacatgacc    2280
accatttgag aaggtctcct aatgtgctga tcttgttatt agctgttata cagtgttttc    2340
ctttcgtcaa aatgactgga gcaaagaggt tattctttga atggttttct cagacagggt    2400
atgtgaagcc attcactaca gtaaaataaa aataataata actcatagaa ctatgagaat    2460
tcatcagcta tggtctgctt agtcctatga ttttgaacaa atcaaaactt ctttggacca    2520
caattttcct agctgaaaaa ttaaacattt ggatcatttg atttctcata tcccttttag    2580
aatatcagtg gcctgtttcc ttggtgcctt tcttttctac cttccctccc catgtgtatc    2640
tgcccttaaa gtagaaagat atgttgacag ctattggtga ggaaaataga caattatgtc    2700
tcccaactga tattcttctc acag                                           2724
```

<210> SEQ ID NO 3
<211> LENGTH: 1228
<212> TYPE: DNA
<213> ORGANISM: Homo sapiens

<400> SEQUENCE: 3

```
gtaagcaaga tggcggtcgg cagttctggg ttagatgaat tagtaaagac attccagcaa        60
tagggaagat tttgtttaga aattggccgc atcttctatt tccactcggt aatttctttt       120
attcttagag cctgaaaagc tgctaaaccc gcacacaaat tttaaaaatt ggaaggaaaa       180
tgataactca tcaggttgcc caaaggccaa aatgttttaa gaagtagatc tagatacaat       240
ttttgtgtta aaggttccta gaggttccat ttgggtaact tgtgtgtgtt cattgaaatg       300
tgtggcaaag agtgtgttct tttggtgctt agtagtggaa tctggaaaga agtttgtca        360 agtgaattga tctttggaat ccttattttc tatgaagatc tttgatgaat acagtgtctt       420
ttttgcattc tgtccctgac tgttctatag aaagacatcc cttgtactct ttagagcaaa       480
gttggtagct cttatggtct tcatttgaat tctaccactg cttcttttc tgtttttaag       540 cccatggtaa cttggggaag ctttgatgc tcttactgtt atttctacta ttatgaaaac       600
tcaggttttc caaacaatc tcaagttgcg gcagtggact gtgagaatag ggggccccct       660
cactccccaa acataagaag tatgtgcttt tcttctttta tctatcccgc tgagatatgt       720
ctatcttatt tggaataaaa gtattatttt tggaaaacag cttttagca ttttaaaat       780 gatgacccaa ctgtcattct cacagcccta gatacaccta atggggaaat gtgagccact       840
taaaagccac ttaaaaacca aagggctttg gaatctatg gcttgagggg tgccttcaga       900
taacaaaaga aaacattcac tacagtaaaa taaaataat aataactcat agaactatga       960
gaattcatca gctatggtct gcttagtcct atgatttga acaaatcaaa acttcttttgg     1020 accacaattt tcctagctga aaaattaaac atttggatca tttgatttct catatccctt      1080
ttagaatatc agtggcctgt ttccttggtg cctttctttt ctaccttccc tccccatgtg      1140
tatctgccct taaagtagaa agatatgttg acagctattg gtgaggaaaa tagacaatta      1200
tgtctcccaa ctgatattct tctcacag                                         1228

<210> SEQ ID NO 4
<211> LENGTH: 129
<212> TYPE: DNA
<213> ORGANISM: Homo sapiens

<400> SEQUENCE: 4
tccaggcaac tcctagtagt acaacggaag aaacagctac ccagaaggaa cagtggtttg        60
gcaacagatg gcatgaggga tatcgccaaa cacccaaaga agactcccat tcgacaacag       120
ggacagctg                                                               129

<210> SEQ ID NO 5
<211> LENGTH: 102
<212> TYPE: DNA
<213> ORGANISM: Homo sapiens

<400> SEQUENCE: 5
atatggactc cagtcatagt ataacgcttc agcctactgc aaatccaaac acaggttgg         60 tggaagattt ggacaggaca ggacctcttt caatgacaac gc                          102

<210> SEQ ID NO 6
<211> LENGTH: 1861
<212> TYPE: DNA
<213> ORGANISM: Homo sapiens

<400> SEQUENCE: 6
gtaatagcct ctgagatttt tatatattat gttttttgaa atccactgag tgactgctga        60
ctatttttct agaaatatgc ccttggtttt agaccaaact actttcctga aggacctgag       120
```

```
gttcttcaaa aattagtttt cttggtagga gtgatactca tattcacctg aatatgaagt    180
tctgagctga aagtaaggaa tttagcagga gggttggcaa agaaaaaac ttattgtcaa     240 aatatatctg tgtgaggcag taagtaatag atatgaaatg aatgttgcca acaataaacg    300
ctaaagaaat tctgagaacc cctccctgcc caccacagca tcacagaaag gtgaattgga    360
cttggtttat gaaaataaa aaaccctgg atagtcagag aaaggaagtg ggtggtgggg      420
gttggtgggg gggcagttt tcctaagaag gagactcctg taaggagaaa cgtgaaggaa    480
gaaaagccaa ggaatgaata tgtcagtgag tggatccatt tttcacaagg gaagatgtgt   540
ttgaatggct aggcaggggc cattatgttg agtgactgaa gtaccacagg cagacccagc   600
acacatgagt ttgcacatgg cagctggagc tctgaggaca cccatggggg aaaaccaagc   660
caggcaaaga tcttcagaat caatattaat tctatgtact gatgaagaga aagagattcc   720
attaaattaa tgaacatgtc aaggacaata caattggctt caactacaca atggtatgat   780
gactcttgaa ggactctact tataagaggg aagatgaaca agagtctaga gcccatcatc   840
aagtgggact ttttctggga gaatgtccat ttgtggtttt gattcaggtt agcacttgct   900
cttgtttgaa atctgggata acagggtcac cacattttg tcctacaaag atctttaata    960
ttttagtgtt gaatatttag tgttgaatct tgaatattta gtgttgaaag gctgcagtgc   1020
agacctgggt acccagtatt ctggtgcttc actgggactg attaaatctc ccccagaggc   1080
agtgatgtgg atagactttg actgaattga cagccagaaa tatcgatggg gtttatgaat   1140
tgtttggcct ctgtttcact caagacttct tatttcagca gagtagatct gtgataactg   1200
ttaaaaacaa catttacaag tatttcagtg aaatttctgc actactcaac attgtacatg   1260
ttaaatttta aagaccgctt atacttgggt ttttgggaag aataattcaa tgacgtccac   1320
tgcttcttat ttcttgcccc tgtatacttt ctgtaactcc acctaggtgg tcttggatga   1380
cgattctgtt tatttgcata ttcactttgt gaagaaaaaa agactaaagg ggggaagagg   1440 gctatttta aaagtcccctt tggttggtaa ggggagggg ataaaatggt gcctgagcca    1500
gcacactttg tcttttctcc atgtgtcaga ttgcatgttt ctataaaaaa ggcaatgttt   1560
ctgtctctct gcaagatttg ggtgttccat catgcactca tgtggagtcc ttccagactc   1620
agcaaaaaca aacacacagc atagctttca tataactcgg cccttcaagg aaagccagtt   1680
acttgttgtg gtgctctttg atgaaacaat aatctatctc agttcgggag atatagtcag   1740
tatgtgcttt ctttcctctt ggccagatgt gaatatttaa aaaaatcagc tgtagaccat   1800
aagccacctt caggtagtgg tttgggaaat caagcaataa cactaatatt gattccttca   1860
g                                                                  1861
```

<210> SEQ ID NO 7
<211> LENGTH: 214
<212> TYPE: PRT
<213> ORGANISM: Artificial Sequence
<220> FEATURE:
<223> OTHER INFORMATION: Humanized Pseudomonas Aeurginosa Exotoxin A
      fragment

<400> SEQUENCE: 7

Met Pro Thr Gly Ala Glu Phe Leu Gly Asp Gly Gly Asp Val Ser Phe
1               5                   10                  15

Ser Thr Arg Gly Thr Gln Asn Trp Thr Val Glu Arg Leu Leu Gln Ala
            20                  25                  30

His Arg Gln Leu Glu Glu Arg Gly Tyr Val Phe Val Gly Tyr His Gly

```
                35                  40                  45
Thr Phe Leu Glu Ala Ala Gln Ser Ile Val Phe Gly Gly Val Arg Ala
    50                  55                  60

Arg Ser Gln Asp Leu Asp Ala Ile Trp Arg Gly Phe Tyr Ile Ala Gly
65                  70                  75                  80

Asp Pro Ala Leu Ala Tyr Gly Tyr Ala Gln Asp Gln Glu Pro Asp Ala
                85                  90                  95

Arg Gly Arg Ile Arg Asn Gly Ala Leu Leu Arg Val Tyr Val Pro Arg
            100                 105                 110

Ser Ser Leu Pro Gly Phe Tyr Arg Thr Ser Leu Thr Leu Ala Ala Pro
        115                 120                 125

Glu Ala Ala Gly Glu Val Glu Arg Leu Ile Gly His Pro Leu Pro Leu
    130                 135                 140

Arg Leu Asp Ala Ile Thr Gly Pro Glu Glu Gly Gly Arg Leu Glu
145                 150                 155                 160

Thr Ile Leu Gly Trp Pro Leu Ala Glu Arg Thr Val Val Ile Pro Ser
                165                 170                 175

Ala Ile Pro Thr Asp Pro Arg Asn Val Gly Gly Asp Leu Asp Pro Ser
            180                 185                 190

Ser Ile Pro Asp Lys Glu Gln Ala Ile Ser Ala Leu Pro Asp Tyr Ala
        195                 200                 205

Ser Gln Pro Gly Lys Pro
    210

<210> SEQ ID NO 8
<211> LENGTH: 416
<212> TYPE: DNA
<213> ORGANISM: Artificial Sequence
<220> FEATURE:
<223> OTHER INFORMATION: Artificial plasmid sequence including fragments
      of CD44 Exon 5 and CD44 Exon 12

<400> SEQUENCE: 8
gtacatcagt cacagacctg cccaatgcct ttgatggacc aattaccata actattgtta      60
accgtgatgg cacccgctat gtccagaaag gagaatacag aacgaatcct gaagacatct    120
accccagcaa ccctactgat gatgacgtga gcagcggctc ctccagtgaa aggagcagca    180
cttcaggagg ttacatcttt tacaccttt ctactgtaca ccccatccca gacgaagaca    240
gtccctggat caccgacagc acagacagaa tccctgctac caatatggac tccagtcata    300
gtataacgct tcagcctact gcaaatccaa acacaggttt ggtggaagat ttggacagga    360
caggacctct ttcaatgaca acgcagcaga gtaattctca gagcttctct acatca        416
```

ALTERNATIVE SPLICING CONSTRUCTS AND METHODS OF USE

CROSS-REFERENCE TO RELATED APPLICATIONS

This patent application claims the benefit of priority to U.S. Provisional Patent Application Ser. No. 61/494,529 filed on Jun. 8, 2011 and entitled "ALTERNATIVE SPLICING CONSTRUCTS AND METHODS OF USE," the subject matter of which is hereby incorporated by reference in its entirety.

REFERENCE TO SEQUENCE LISTING

The sequence listing submitted herewith as a text file named "10021.00014USU1_Sequence_Listing_ST25" created on May 31, 2012, and having a size of 11,811 bytes is hereby incorporated by reference pursuant to 37 C.F.R. §1.52 (e)(5).

FIELD OF THE INVENTION

The present invention is related to alternative splicing nucleotide constructs and their use for treating diseases such as cancer and for studying the molecular mechanisms of splicing.

BACKGROUND OF THE INVENTION

It is estimated that the human body may contain over two million proteins, yet these two million proteins are encoded by approximately only 20,000 to 25,000 genes. The discrepancy between the amount of proteins and the genes encoding those proteins can be explained by genes (or germline DNA) that contain a multitude of different coding sequences (exons) that are interspersed with non-coding sequences (introns) and how the splicing process takes copies of this germline DNA apart and puts it back together again. During the process of transcription, the genetic information in a DNA molecule is transferred to a primary RNA transcript. A primary RNA transcript is a copy of the DNA molecule in that it also contains exons interspersed with introns. The primary RNA transcript is then processed via "cutting out" introns, and many of the exons as well, and re-joining the pieces to create a messenger RNA (mRNA) with a unique combination of exons. The mRNA is then translated into a protein.

The term used to describe the cutting and re-joining process is "splicing." Based upon where the splices are made, many different mRNA sequences and thus different proteins can be made from the transcription of a single piece of germline DNA. FIG. 1 shows, for example, how alternative splicing of a single primary antibody RNA transcript can result in the production of antibodies that differ from one another.

Splicing takes place in a large complex, the spliceosome, which contains approximately 200 proteins and 5 small RNAs (U snRNAs) (See Wachtel and Manely, Mol. BioSyst, 5:311-316 (2009)). Accordingly, there are likely a large number of factors that control which exons are spliced out and which remain, and many of these factors continue to be poorly understood. There continues to be a general need in the art for the development of splicing constructs, cell lines and assays that can be used to elucidate these factors and their mechanisms of action. There is also a specific need to elucidate the mechanism of splicing specific constructs such as those associated with CD44.

CD44 is a glycoprotein and a cell-adhesion protein. CD44 has also been implicated as a lymphocyte homing receptor. The CD44 human gene contains 20 exons, 10 of which encode the membrane proximal extracellular domain (See Fox et al., Cancer Research 54:4539-4546 (1994)). These 10 exons have been termed v1-v10. At least 20 different isoforms of CD44 have been described that result from the differential, or alternative, splicing of these 10 exons. Id. at 4539.

Importantly, the CD44 variant domain 6 (CD44v6) isoform has been implicated in tumorigenesis, tumor cell invasion, and tumor metastasis (See Heider et al., Cancer Immunol. Immunother. 53:567-579, 567 (2004)). Intense and homogeneous expression of CD44v6 was reported for the majority of squamous cell carcinomas and a portion of adenocarcinomas of differing origin. Id. at 567. Nevertheless, the splicing mechanism of action that results in the production of CD44v6 remains poorly understood and there is a need in the art for alternative splicing constructs and cell lines that can be used to study the mechanisms of CD44v6 splicing specifically.

In addition to CD44, other splice variant proteins such as MDM2, BRCA1/BRCA2, PSA and numerous members of the FGF receptor family have been reported to be differentially expressed in tumor cells when compared to their normal counterparts (See Brinkman, B. M., Clin. Biochem. 37:584-594 (2004)). Since alternative splicing has been associated with the development and/or progression of several cancers, researchers have suggested the use of alternative splicing as a means of targeting the expression of therapeutic genes to tumor cells in vivo (See Hayes et al., Cancer Gene Therapy 9:133-141 (2002)).

Hayes et al. suggest the use of a splice activated gene expression vector using the CD44 isoform R1 that is selectively active in tumor cells and produces alkaline phosphatase. CD44R1 contains contiguous variant domain 8, variant domain 9, and variant domain 10. Once the alkaline phosphatase is produced by the tumor cell according the methods of Hayes et al., an inactive pro-drug, etoposide phosphatase, is administered to the tumor cell. The alkaline phosphatase is excreted from the tumor cell and acts on the inactive pro-drug to create the active drug, etoposide. The etoposide then kills the tumor cell that produced the alkaline phosphatase as well as the surrounding cells. The Hayes et al. article notes that a benefit of their system is the greatly enhanced efficacy of the treatment due to the diffuse nature of the pro-drug. Since the pro-drug is located outside the tumor cell and the drug activator is excreted from the cell, the toxic effect occurs outside the tumor cell and allows for bystander cell killing. Id. at 139. In other words, the Hayes et al. system allows for killing of tumor cells and other non-tumor cells that do not splice the CD44R1 alternative splicing construct nor express the alkaline phosphatase.

While bystander killing could be beneficial in certain instances, there is a need in the art for alternative splicing constructs that do not require secretion of a pro-drug activator and an additional administration of a pro-drug to achieve tumor cell killing. There is also a need for alternative splicing constructs that work in tumor cells that will not splice the CD44R1 construct described in Hayes et al. Splicing of the CD44R1 construct is limited to those cells that express CD44R1 naturally. Accordingly, there is a need in the art to provide other alternative splicing constructs and their uses for cancer treatment that 1) do not require multiple administrations of pro-drugs, 2) do not result in extensive bystander cell killing, and 3) function in cells other than those cells that express CD44R1 naturally. As mentioned above, there is also a need to develop assays, including high-throughput assays, that allow for the study of these other alternative splicing constructs.

SUMMARY OF THE INVENTION

The present invention answers the need for new alternative splicing constructs and new methods of using these alternative splicing constructs for the study of splicing mechanisms and compounds that affect splicing. In particular, the present invention provides an alternative splicing construct comprising a promoter operably linked to the following in a 5' to 3' order: a CD44 exon 5 or a fragment thereof, an intervening nucleic acid sequence containing one or more stop codons, a variable CD44 exon or a fragment thereof, and a nucleic acid sequence encoding a toxin protein or an indicator protein. In some embodiments of the present invention, the alternative splicing construct is a CD44v6 alternative splicing construct comprising a CD44 exon 5, a CD44 intron 9-10 nucleotide sequence, and a CD44 exon 10 sequence. FIG. 2A shows a schematic of a general construct containing these elements in addition to a toxin, or an indicator protein such as GFP or an epitope tag. Also described herein is a CD44v8 alternative splicing construct comprising a CD44 exon 5, a CD44 intron 11-12 nucleotide sequence, and a CD44 exon 12 sequence. FIG. 18 shows several examples of CD44v8 alternative splicing constructs.

Such CD44v6 and CD44v8 based alternative splicing constructs can be transfected into target cells and potentially other non-target cells. The target cells are chosen based upon their selective ability to splice the CD44v6 alternative splicing construct and thereby selectively express the encoded toxin or indicator protein. Upon splicing and expression of the toxin, the target cells undergo cell death, whereas the non-target cells that do not splice the construct and do not express the toxin largely remain viable. The present invention thereby provides for directed tumor cell killing via the expression of a toxin within the tumor cells themselves. These toxins have cytotoxic effects focused upon those tumor cells that contain and express the alternative splicing construct. While there may be limited cytotoxic effect to surrounding cells upon tumor cell death, these effects are greatly diminished as compared to the methods described in the prior art.

In the alternative, splicing and expression of an indicator protein in a cell allows for testing of splicing mechanisms and the effect of different compounds on splicing in that cell. The present invention includes methods of testing for pre-mRNA splicing in a cell comprising:
  a. providing the cell comprising an alternative splicing construct, wherein the splicing construct comprises a promoter operably linked to, in 5' to 3' order, a CD44 exon 5 or a fragment thereof, an intervening nucleic acid sequence containing one or more stop codons, a variable CD44 exon or a fragment thereof, and a nucleic acid sequence encoding an indicator protein;
  b. transcribing a pre-mRNA sequence from the splicing construct; and
  c. testing for splicing, wherein expression of the indicator protein at a level above a control expression level indicates splicing.

Also included are methods of determining the effect of a compound on pre-mRNA splicing wherein the compound is administered to the cell prior to step b. above. The alternative splicing constructs of the present invention that encode a fluorescent indicator protein provide accurate and quantifiable evidence of splicing events since the fluorescent protein is only expressed upon the splicing of the construct. These methods and constructs can be used to identify splicing activators, inhibitors, and the like.

BRIEF DESCRIPTION OF THE FIGURES

FIG. 2A is a schematic representation of a general alternative splicing construct of the present invention wherein the construct contains CD44v6 Exons 5 and 10 interspersed with an intron as an intervening nucleic acid sequence, and wherein Exon 10 is adjacent to a nucleotide sequence encoding any one of a toxin, GFP or epitope tag. FIG. 2B shows the results of RT-PCR that, along with sequencing, confirms splicing and removal of a CD44v6 Intron 9-10 from a test construct pDD826 in MCF-7 cells to result in an RNA transcript wherein Exon 5 and Exon 10 are in-frame;

FIGS. 11A-11B provide a southern blot analysis (FIG. 11A) and the results of DNA sequencing (FIG. 11B), which demonstrate proper splicing of CD44v8 alternative splicing construct pDD888;

FIGS. 12A-12B contain southern blot analyses which demonstrate CD44v6 and CD44v8 expression in K562 leukemia cells (FIG. 12A) and proper splicing of CD44v6 (pDD826) and CD44v8 (pDD888) alternative splicing constructs (FIG. 12B);

FIGS. 16A-16D provide a southern blot analysis (FIG. 16A), a graphical representation (FIG. 16B), and photographs showing the results of fluorescent microscopy (FIGS. 16C and 16D), all of which demonstrate stable expression of a GFP-linked CD44v6 alternative splicing construct in MCF-7 breast cancer cells;

FIG. 17 is a graphic representation of data showing the results of a plate-based splicing assay using MCF-7 cells that stably express a GFP-linked CD44v6 alternative splicing construct.

DETAILED DESCRIPTION OF THE INVENTION

Figure 1:
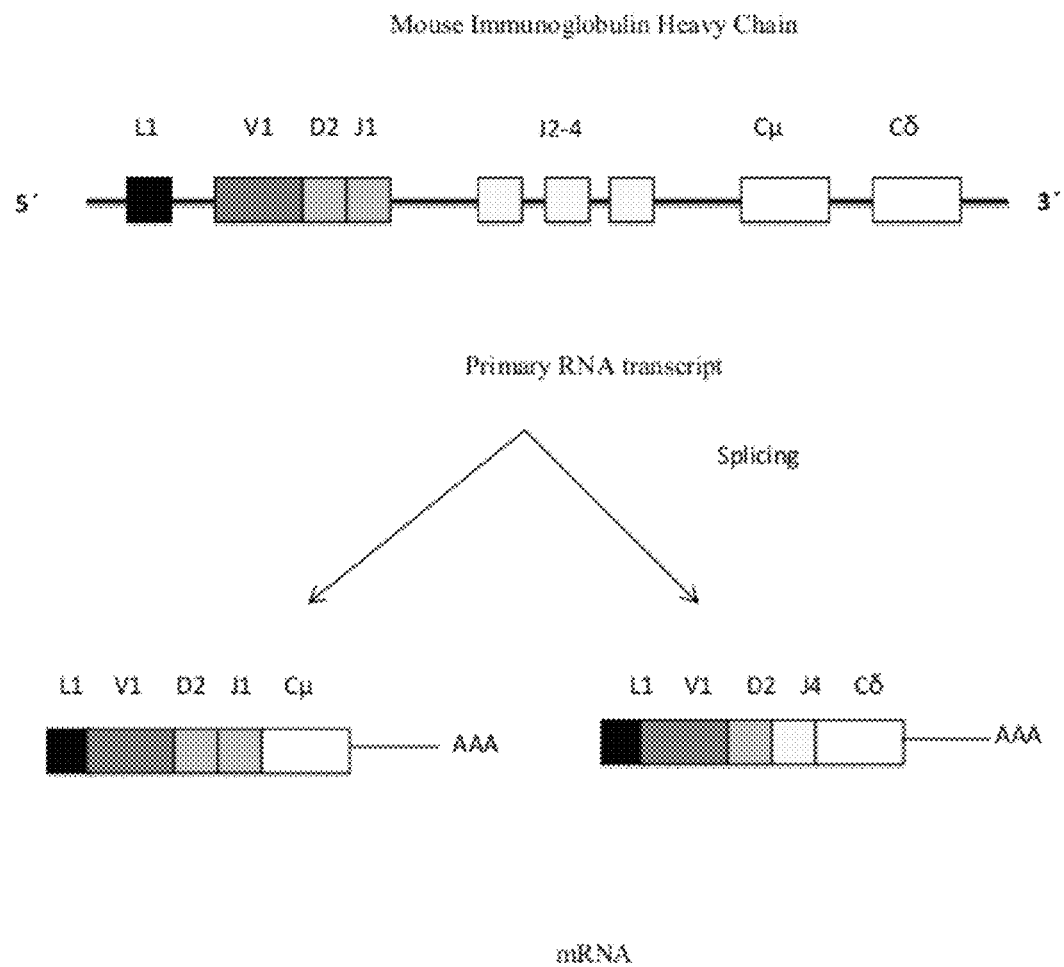
FIG. 1 is a schematic representation of a primary RNA transcript of mouse immunoglobulin (antibody) heavy chain that is differentially spliced to produce two different mRNA transcripts that encode the μ and δ heavy chains.
Figure 3A:
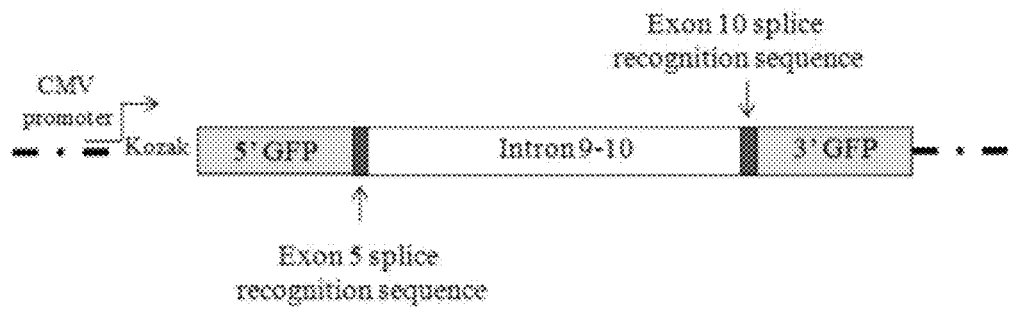
FIGS. 3A and 3B are schematic representations of alternative splicing constructs of the present invention wherein a nucleic acid sequence encoding a green fluorescent protein (GFP) (FIG. 3A) or a toxin (FIG. 3B) is split by a CD44v6 Intron 9-10.
Figure 3B:
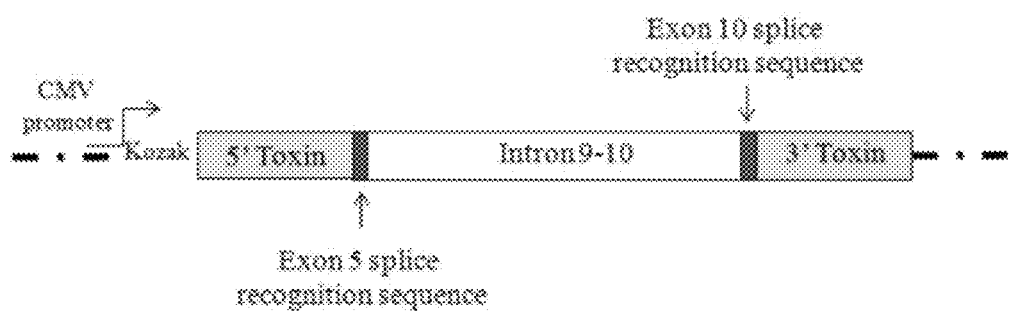

The present invention provides an alternative splicing construct comprising a promoter operably linked to, in 5' to 3' order, a CD44 exon 5 or a fragment thereof, an intervening nucleic acid sequence containing one or more stop codons, a variable CD44 exon or a fragment thereof, and a nucleic acid sequence encoding a toxin protein or an indicator protein. In other embodiments, an alternative splicing construct comprises a promoter operably linked to the following in a 5' to 3' order: a 5' fragment of a nucleic acid sequence encoding a toxin or an indicator protein, a first splice recognition sequence, a second splice recognition sequence, and a complementary 3' fragment of the nucleic acid sequence encoding the toxin or indicator protein, wherein the 5' and 3' portions of the toxin or indicator protein encoding nucleic acid sequences are not themselves translated into functional proteins or peptides. FIG. 3B shows a schematic of a construct containing these elements. As used herein, the term "alternative splicing construct" refers to any polynucleotide construct that can be spliced and translated into a protein that comprises a toxin or an indicator protein in a subset of cells. Exemplary subsets of cells are provided below.

In one embodiment, the alternative splicing construct is a plasmid construct comprising deoxyribonucleic acid sequences (DNA). In other embodiments, the alternative splicing construct is a viral vector construct, such as an adenovirus, adeno-associated virus, alphavirus, herpesvirus, retrovirus, lentivirus or vacciniavirus, a linear DNA construct, or an RNA construct.

The term "CD44" refers to a family of cell-surface glycoproteins that are expressed on a variety of cells. CD44 proteins are encoded by a gene that is well conserved and that contains 20 exons. The CD44 exons are distributed in the gene in four regions: 1) a constant region consisting of exons 1-5, 2) a central region that spans exons 6a-14, also known as variable exons v1-v10, 3) a constant region consisting of exons 15-17, which are subject to general constitutive splicing, and 4) a region composed of exons 18 and 19, which show an alternate use of a short or long cytoplasmic tail, respectively. See, Vela, E. et al., RNA 13:2312-2323 (2007).

As used herein, a "CD44 exon 5" includes all nucleotide sequences that correspond to approximately the fifth chromosomal CD44 constant exon region that immediately precedes a span of variable chromosomal CD44 exon regions such as variable human CD44 Exons 6a-14. In one embodiment, the CD44 exon 5 has a sequence of SEQ ID NO:1 or a fragment thereof. A fragment can contain approximately 10, 20, 30, 50 or 100 nucleotides of SEQ ID NO:1. The term "variable CD44 exon" refers to any nucleotide sequence that corresponds to a CD44 exon amongst a group of CD44 exons, which group undergoes variable splicing. Exemplary variable CD44 exons are human CD44 exons 6a, 6, 7, 8, 9, 10, 11, 12, 13 and 14. These variable human CD44 exons are also termed v1, v2, v3, v4, v5, v6, v7, v8, v9 and v10, respectively. In one embodiment, the variable CD44 exon is a CD44 exon 10. A preferred CD44 exon 10 is a human CD44 exon 10 having a sequence as shown in SEQ ID NO:4 or a fragment thereof. A fragment can contain approximately 10, 20, 30, 50 or 100 nucleotides of SEQ ID NO:4. In another embodiment, the variable CD44 exon is a CD44 exon 12. A preferred CD44 exon 12 is a human CD44 exon 12 having a sequence as shown in SEQ NO:5 or a fragment thereof. A fragment can contain approximately 10, 20, 30, 50 or 100 nucleotides of SEQ ID NO:5.

The "intervening nucleic acid sequence" in the alternative splicing construct is any contiguous stretch of nucleotides that contains one or more stop codons. The presence of these one or more stop codons ensure that the toxin or indicator protein is only expressed upon removal of the intervening nucleic acid sequence via splicing, and accordingly, ensure that toxin or indicator protein production only occurs in those cells capable of recognizing and splicing the first and second splice recognition sequences. The intervening nucleic acid sequence can also contain the first splice recognition sequence at a location more 5' than the one or more stop codons. In these instances, the first splice recognition sequence can be, but is not limited to, a splice dinucleotide selected from GT-AG and GC-AG.

Exemplary intervening nucleic acid sequences are CD44 intron sequences including, but not limited to, CD44 intron 5-6, CD44 intron 6-7, CD44 intron 7-8, CD44 intron 8-9, CD44 intron 9-10, CD44 intron 10-11, CD44 intron 11-12, CD44 intron 12-13, CD44 intron 13-14, and fragments thereof. In one embodiment, a human CD44 intron 9-10 has a nucleotide sequence of SEQ ID NO:2. In another embodiment, a human CD44 intron 11-12 has a nucleotide sequence of SEQ ID NO:6. Also encompassed are intervening nucleic acid sequences that are fragments of CD44 introns, preferably, 3' fragments of CD44 introns. In one embodiment, the intervening nucleic acid sequence contains a human CD44 intron 9-10 fragment having a nucleotide sequence of SEQ ID NO:3. In some embodiments, the alternative splicing construct comprises approximately 100, 250, 500, 1000 or 1500 of the 3' nucleotides of SEQ ID NO:2 or SEQ ID NO:6.

As used herein, the term "splice recognition sequence" refers to any combination of nucleotides that are recognized or acted upon by any spliceosome, or any portion of a spliceosome, to achieve cutting, ligating or splicing of an oligonucleotide construct containing those splice recognition sequences. This combination of nucleotides can be contiguous or not. In some embodiments, the splice site recognition sequence comprises one or more of the following deoxyribonucleotide sequence motifs: 1) "ag|GTragt" wherein "|" is the splice junction and "r" is a or g, and 2) "(y)$_{12-17}$nAG|g" wherein "|" is the splice junction, wherein "y" is c or t and "n" is a, t, g or c, and wherein the subscript indicates the repeat number. See Shimada et al., BMC Evolutionary Biology 10:122 (2010). The splice recognition sequences may further comprise nucleotide sequences in addition to those sequences provided above as 1) and 2). The present invention also encompasses RNA vectors having ribonucleotide motifs complementary to those deoxyribonucleotide sequence motifs provided above. In any of these embodiments, the splice recognition sequence motif comprises sequence motif 1) or sequence motif 2) above and between 1-5, 1-10, 1-20, 1-30, 1-40, or 1-50 additional nucleotides that are necessary for splicesome recognition, cutting, ligating and/or splicing at the splice junction.

As noted above, the term "alternative splicing construct" refers to any polynucleotide construct that can be spliced and translated into a protein comprising a toxin or an indicator protein in a subset of cells. In some embodiments, the subset of cells is cancer cells, and more preferably cancer cells that express a particular isoform of a protein. A "cancer" is defined herein as any cell or group of cells undergoing abnormal or excessive cell division. Cancer includes, but is not limited to, acute lymphoblastic leukemia, acute myeloid leukemia, adrenocortical carcinoma, basal cell carcinoma, bladder cancer, brain cancer, breast cancer, Burkitt's lymphoma, carcinoid tumor, cerebellar astrocytoma, cervical cancer, chronic lymphocytic leukemia, chronic myelogenous leukemia, colon cancer, cutaneous T-cell lymphoma, endometrial cancer, esophageal cancer, intraocular melanoma, retinoblastoma, gallbladder cancer, gastric cancer, gastrointestinal stromal tumor, gestational trophoblastic tumor, glioma, hairy cell leukemia, head and neck cancer, heart cancer, liver cancer, hypopharyngeal cancer, intraocular melanoma, islet cell carcinoma, Kaposi sarcoma, kidney cancer, laryngeal cancer, leukemia, liposarcoma, lung cancer, macroglobulinemia, medulloblastoma, melanoma, mesothelioma, myeloid leukemia, nasopharyngeal carcinoma, neuroblastoma, oral cancer, oropharyngeal cancer, ovarian cancer, pancreatic cancer, parathyroid cancer, pituitary adenoma, prostate cancer, renal cell carcinoma, retinoblastoma, rhabdomyosarcoma, skin cancer, small lung cell cancer, small intestine cancer, squamous cell carcinoma, stomach cancer, testicular cancer, throat cancer, thymoma, thyroid cancer, trophoblastic tumor, urethral cancer, uterine cancer, vaginal cancer, and vulvar cancer. In some embodiments, the cancer is a squamous cell carcinoma (i.e., head, neck, eosophagus, lung, skin, cervix or vulva), an adenocarcinoma (i.e., breast, Barrett's eosophagus, lung, gastric, pancreas, colon/rectum, endometrium, uterine, or prostate), a thyroid carcinoma, a small cell lung cancer, a renal carcinoma, urinary bladder tumor, clear cell ovarian cancer, basal cell carcinoma, acute myelogenous leukemia, non-Hodgkin's lymphoma, cutaneous lymphoma, multiple myeloma, diffuse large B cell lymphoma, Hodgkin's lymphoma, or any cancer described in Heider et al., Cancer Immunol. Immunother. 53:567-579 (2004). In one embodiment, the cell is an MCF-7 leukemia cell.

In some embodiments of the present invention, the alternative splicing construct is a CD44v6 alternative splicing construct comprising a CD44 exon 5, a CD44 intron 9-10 nucleotide sequence, a CD44 exon 10 sequence, and a toxin or indicator encoding sequence. As mentioned above, FIG. 2A shows a schematic of a general construct containing these elements in addition to a toxin, or an indicator protein such as GFP or an epitope tag. In one embodiment, the CD44 exon 5 nucleotide sequence comprises SEQ ID NO:1, the CD44 intron 9-10 nucleotide sequence comprises SEQ ID NO:2 or SEQ ID NO:3, and the CD44 exon 10 nucleotide sequence comprises SEQ ID NO:4. Accordingly, the present invention includes an alternative splicing construct comprising the following in a 5' to 3' order: a promoter operably linked to SEQ ID NO:1, SEQ ID NO:2, SEQ ID NO:4, and a nucleotide sequence encoding a toxin or an indicator protein. In other embodiments, the alternative splicing construct comprises the following in a 5' to 3' order: a promoter operably linked to SEQ ID NO:1, SEQ ID NO:3, SEQ ID NO:4, and a nucleotide sequence encoding a toxin or an indicator protein.

In some embodiments, the CD44 exon 5 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:1, the CD44 intron 9-10 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:2 or SEQ ID NO:3, and the CD44 exon 10 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:4.

Also described herein is a CD44v8 alternative splicing construct comprising a CD44 exon 5, a CD44 intron 11-12 nucleotide sequence, a CD44 exon 12 sequence, and a toxin or indicator encoding sequence. In one embodiment, the CD44 exon 5 nucleotide sequence comprises SEQ ID NO:1, the CD44 intron 11-12 nucleotide sequence comprises SEQ ID NO:6, and the CD44 exon 12 nucleotide sequence comprises SEQ ID NO:5. Accordingly, the present invention includes an alternative splicing construct comprising the following in a 5' to 3' order: a promoter operably linked to SEQ ID NO:1, SEQ ID NO:6, SEQ ID NO:5, and a nucleotide sequence encoding a toxin or an indicator protein.

In some embodiments, the CD44 exon 5 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:1, the CD44 intron 11-12 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:6, and the CD44 exon 12 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:5.

It should be understood that the alternative splicing construct of the present invention can contain any portion of a CD44 exon 5 nucleotide sequence that contains a first splice site recognition sequence. In one embodiment, the alternative splicing construct comprises a 3' fragment of SEQ ID NO:1. The 3' fragment can contain 50%, 40%, 30%, 20%, 10%, 5%, 4%, 3%, 2% or 1% of the 3' half of SEQ ID NO:1. In some embodiments, the alternative splicing construct comprises between 5-10, 5-15, 5-20 or 5-30 of the 3' nucleotides of SEQ ID NO:1.

It should be further understood that the alternative splicing construct of the present invention can contain any portion of a CD44 exon 10, CD44 exon 12, CD44 intron 9-10, or CD44 intron 11-12 nucleotide sequence that contains a second splice site recognition sequence. In one embodiment, the alternative splicing construct comprises a 3' fragment of SEQ ID NO:2 or SEQ ID NO:3. The 3' fragment can contain 50%, 40%, 30%, 20%, 10%, 5%, 4%, 3%, 2%, 1%, 0.5% or 0.25% of the 3' half of SEQ ID NO:2 or SEQ ID NO:3. In some embodiments, the alternative splicing construct comprises between 5-10, 5-15, 5-20, or 5-30 of the 3' nucleotides of SEQ ID NO:2 or SEQ ID NO:3. In other or further embodiments, the alternative splicing construct comprises a 5' fragment of SEQ ID NO:4. The 5' fragment can contain 50%, 40%, 30%, 20%, 10%, 5%, 4%, 3%, 2% or 1% of the 5' half of SEQ ID NO:4. In some embodiments, the alternative splicing construct comprises between 5-10, 5-15, 5-20, or 5-30 of the 5' nucleotides of SEQ ID NO:4. In still other or further embodiments, the alternative splicing construct comprises a 5' fragment of SEQ ID NO:5. The 5' fragment can contain 50%, 40%, 30%, 20%, 10%, 5%, 4%, 3%, 2% or 1% of the 5' half of SEQ ID NO:5. In some embodiments, the alternative splicing construct comprises between 5-10, 5-15, 5-20, or 5-30 of the 5' nucleotides of SEQ ID NO:5. In yet other or further embodiments, the alternative splicing construct comprises a 5' fragment of SEQ ID NO:6. The 5' fragment can contain 50%, 40%, 30%, 20%, 10%, 5%, 4%, 3%, 2% or 1% of the 5' half of SEQ ID NO:6. In some embodiments, the alternative splicing construct comprises between 5-10, 5-15, 5-20, or 5-30 of the 5' nucleotides of SEQ ID NO:6.

According to the present invention, an alternative splicing construct is provided that comprises a promoter operably linked to the following in a 5' to 3' order: a CD44 exon 5 or a fragment thereof, an intervening nucleic acid sequence containing one or more stop codons, a variable CD44 exon or a fragment thereof, and a nucleic acid sequence encoding a toxin protein or an indicator protein. The promoter can be any promoter known to one of skill in the art which includes both constitutive and inducible promoters. Exemplary promoters include those described in Ogawa et al., BioTechniques 42:628-633 (2007). The promoters described in Ogawa et al. include "clone 6" described therein that comprises three NFκB binding motifs arranged in reverse, followed by a TATA box from the human heme oxygenase I gene. Additional exemplary promoters may be found in the Eukaryotic Promoter Database (EPD) as developed by the Swiss Institute of Bioinformatics.

The nucleic acid sequence encoding a toxin that comprises a portion of an alternative splicing construct can encode any toxin appropriate for the objects of the present invention. The toxin can be selected from the group consisting of; cholera toxin, diphtheria toxin, shiga toxin, P. aeuroginosa exotoxin A, aerolysin, perfringolysin, listeriolysin O, pnuemolysin, streptolysin O, lethal factor from B. anthracis, nucleases, ribonucleases, any of neurotoxins A-G, tetanus toxin or any other appropriate toxin described in Schmitt, C. K. et al. Emerging Infectious Diseases, 5:2:224-234 (1999). It should be understood that the terms "toxin" and "toxin protein" encompass all peptides and proteins that maintain some toxic activity in the target cells. Accordingly, the toxin can be a portion of a chimeric protein that also comprises a protein encoded by an exon in the alternative splicing construct. In some embodiments, the toxin and a protein corresponding to exon 10 of CD44, or a fragment thereof, are fused together as a chimeric protein. In other embodiments, the toxin is produced following the joining of two nucleotide sequences encoding toxin halves during splicing.

Instead of a toxin nucleotide sequence, the alternative splicing constructs can include a nucleotide sequence that encodes an indicator protein. As used herein, the term "indicator protein" includes any protein whose expression can be detected and compared to a control level of expression. As used herein, the term "indicator protein" includes, but is not limited to, a fluorescent protein. The fluorescent protein can be any known to one of skill in the art including, but not limited to, a green fluorescent protein (GFP), a yellow fluorescent protein (YFP), a red fluorescent protein (RFP), and a cyan fluorescent protein (CFP). FIG. 3 shows one embodiment of an alternative splicing construct that contains a fluorescent reporter sequence that encodes the fluorescent protein. The term "expression" is defined herein to at least include translation of an mRNA polynucleotide sequence into a polypeptide sequence.

The term "peptides" is generally defined to mean chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" refers to an amino acid (D or L) or an amino acid mimetic incorporated in an oligopeptide by an amide bond or amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and;
6) Phenylalanine (F), Tyrosine (Y), Tryptophan (W).

The alternative splicing constructs of the present invention comprise a promoter operably linked to the following in a 5' to 3' order: a CD44 exon 5 or a fragment thereof, an intervening nucleic acid sequence containing one or more stop codons, a variable CD44 exon or a fragment thereof, and a nucleic acid sequence encoding a toxin protein or an indicator protein. These splicing constructs can further contain any additional nucleotide sequences that improve transcription, splicing or translation of the alternative splicing construct. Exemplary sequences that can be added are as follows: a Kozak sequence and a methionine initiation codon.

In addition to alternative splicing constructs, the present invention includes methods of using the alternative splicing constructs. The alternative splicing constructs can be used for achieving targeted cell death in various cells types, for determining the effect of compounds on splicing in various cell types, and for the study of splicing mechanisms generally. As used herein, the term "targeted cell" refers to any cell that is desired to undergo cell death. In some embodiments, the targeted cell is a cancer cell. Targeted cell death may be determined by any means known to those of skill in the art and is evidenced in certain methods by a reduction in tumor size or mass, increased tumor necrosis, induction of apoptosis, and/or reduced cell viability. Exemplary methods that can be used to measure targeted cell death are the MTT and TUNEL methods as described in Mosmann, T., J. Immunol. Methods 65(1-2):55-63 (1983) and Negoescu, A. et al. Biomed Pharmacother 52(6):252-8 (1998), respectively.

The present invention takes advantage of the fact that many cell receptors and other proteins are alternatively spliced in tumor cells, but not in non-tumor cells. Thus, the alternative splicing constructs can be administered generally to a group of cells, taken up indiscriminantly by those cells, yet only spliced by the tumor cells within that group. The present invention's novel approach of associating this selective splicing with the expression of a toxin within the tumor cell provides for selective destruction of tumor cells, without the need for selective cell uptake of the alternative splicing construct containing the toxin. These methods can be expanded to include not only tumor cells, but any other cell that is undesired and that exhibits selective splicing of a particular germline DNA sequence. An advantage of these embodiments is that the toxin is expressed within the cell that is targeted for cell death. This invention does not require separate administrations of pro-drugs or other agents to achieve targeted cell death. The present invention also advantageously limits bystander, or non-tumor, cell killing.

The definitions relating to the components of the alternative splicing construct provided above, apply equally to those alternative splicing constructs used in the methods described herein for achieving targeted cell death in a cell or a group of cells. In some embodiments, the alternative splicing construct used in the targeted cell death methods is a CD44v6 alternative splicing construct comprising a CD44 exon 5, a CD44 intron 9-10 nucleotide sequence, a CD44 exon 10 sequence, and a toxin encoding sequence. In one embodiment, the CD44 exon 5 nucleotide sequence comprises SEQ ID NO:1, the CD44 intron 9-10 nucleotide sequence comprises SEQ ID NO:2 or SEQ ID NO:3, and the CD44 exon 10 nucleotide sequence comprises SEQ ID NO:4. In other embodiments, the alternative splicing construct used in the targeted cell death methods is a CD44v8 alternative splicing construct comprising a CD44 exon 5, a CD44 intron 11-12 nucleotide sequence, and a CD44 exon 12 sequence, and a toxin encoding sequence. In one embodiment, the CD44 exon 5 nucleotide sequence comprises SEQ ID NO:1, the CD44 intron 11-12 nucleotide sequence comprises SEQ ID NO:6, and the CD44 exon 12 nucleotide sequence comprises SEQ ID NO:5.

An alternative splicing construct can also be administered to a cell or a group of cells, which construct comprises a CD44 exon 5 nucleotide sequence that has approximately 99%, 98%, 97%, 96%, 95%, 94%, 93%, 92%, 91%, 90%, 85%, 80%, 75%, 70%, 60%, 50%, or 40% sequence homology with SEQ ID NO:1, a CD44 intron 9-10 nucleotide sequence that has approximately 99%, 98%, 97%, 96%, 95%, 94%, 93%, 92%, 91%, 90%, 85%, 80%, 75%, 70%, 60%, 50%, or 40% sequence homology with SEQ ID NO:2 or SEQ ID NO:3, and a CD44 exon 10 nucleotide sequence that has approximately 99%, 98%, 97%, 96%, 95%, 94%, 93%, 92%, 91%, 90%, 85%, 80%, 75%, 70%, 60%, 50%, or 40% sequence homology with SEQ ID NO:4.

An alternative splicing construct can be administered to a cell or a group of cells, which construct comprises CD44 exon 5 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:1, the CD44 intron 11-12 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:6, and the CD44 exon 12 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:5.

It should be understood that the alternative splicing construct used in the methods of the present invention can contain any portion of a CD44 exon 5 nucleotide sequence that contains a first splice site recognition sequence. In one embodiment, an alternative splicing construct is administered to a cell or a group of cells in order to achieve targeted cell death, which construct comprises a 3' fragment of SEQ ID NO: 1. The 3' fragment can contain 50%, 40%, 30%, 20%, 10%, 5%, 4%, 3%, 2% or 1% of the 3' half of SEQ ID NO: 1. In some embodiments, the alternative splicing construct comprises between 5-10, 5-15, 5-20 or 5-30 of the 3' nucleotides of SEQ ID NO: 1.

It should be further understood that an alternative splicing construct administered according to the methods of the present invention can contain any portion of a CD44 exon 10, CD44 exon 12, CD44 intron 9-10, and/or CD44 intron 11-12 nucleotide sequence that contains a second splice site recognition sequence. In one embodiment, the alternative splicing construct that is administered to a cell or a group of cells, which construct comprises a 3' fragment of SEQ ID NO:2, SEQ ID NO:3, or SEQ ID NO:6. The 3' fragment can contain 50%, 40%, 30%, 20%, 10%, 5%, 4%, 3%, 2%, 1%, 0.5% or 0.25% of the 3' half of SEQ ID NO:2, SEQ ID NO:3, or SEQ ID NO:6. In some embodiments, the alternative splicing construct comprises between 5-10, 5-15, 5-20, or 5-30 of the 3' nucleotides of SEQ ID NO:2, SEQ ID NO:3, or SEQ ID NO:6. In another embodiment, the alternative splicing construct that is administered to a cell or a group of cells, which construct comprises a 5' fragment of SEQ ID NO:4 or SEQ ID NO:5. The 5' fragment can contain 50%, 40%, 30%, 20%, 10%, 5%, 4%, 3%, 2% or 1% of the 5' half of SEQ ID NO:4 or SEQ ID NO:5. In some embodiments, the alternative splicing construct comprises between 5-10, 5-15, 5-20, or 5-30 of the 5' nucleotides of SEQ ID NO:4 or SEQ ID NO:5.

The compositions described herein are also contemplated to include pharmaceutical compositions comprising alternative splicing constructs and at least one of any suitable auxiliary such as, but not limited to, mpoules, binder, stabilizer, buffers, salts, lipophilic solvents, preservative, or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, 18$^{th}$ Edition, Mack Publishing Co. (1990)). Pharmaceutically acceptable carriers can be routinely selected that are suitable for the mode of administration, solubility and/or stability of the compound. Pharmaceutical excipients and additives useful in the present invention include, but are not limited to, proteins, peptides, amino acids, lipids, and carbohydrates. The pharmaceutical compositions comprising the compounds of the present invention can also include a buffer or a pH-adjusting agent. Additionally, pharmaceutical compositions of the invention can include polymeric excipients/additives Pharmaceutical compositions can be in the form of a tablet or capsule, such as discrete units such as capsules, cachets or tablets each containing a predetermined amount of the alternative splicing constructs; as a powder or granules; as a solution or a suspension in an aqueous liquid or a non-aqueous liquid; or as an oil-in-water liquid emulsion or a water-in-oil emulsion and as a bolus, etc. A tablet may be made by compression or molding, optionally with one or more accessory ingredients. The tablets may be optionally coated or scored and may be formulated so as to provide a slow or controlled release of the active ingredient therein.

Formulations suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The formulations may be presented in unit-dose or multi-dose containers, for example, sealed mpoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the alternative splicing constructs to be administered in a suitable liquid carrier. The liquid forms may include suitably flavored suspending or dispersing agents such as the synthetic and natural gums, for example, tragacanth, acacia, methyl-cellulose and the like. Formulations for rectal administration may be presented as a suppository with a suitable base comprising, for example, cocoa butter or a salicylate. Formulations suitable for vaginal administration may be presented as pessaries, tamports, creams, gels, pastes, foams or spray formulations containing in addition to the active ingredient such carriers as are known in the art to be appropriate.

The compositions of the present invention may also be entrapped in microcapsules prepared, for example, by coacervation techniques or by interfacial polymerization, for example, hydroxymethylcellulose or gelatin-microcapsules and poly (methylmethacylate) microcapsules, respectively, in colloidal drug delivery systems (for example, liposomes, albumin microspheres, microemulsions, nanoparticles and nanocapsules) or in macroemulsions. REMINGTON'S PHARMACEUTICAL SCIENCES (Gennaro, 18$^{th}$ Edition, Mack Publishing Co. (1990)).

The present invention provides stable formulations as well as preserved solutions and formulations containing a preservative as well as multi-use preserved formulations suitable for pharmaceutical or veterinary use, comprising the alternative splicing constructs disclosed herein in a pharmaceutically acceptable formulation. In general, the compositions disclosed herein may be used alone or in concert with therapeutic agents at appropriate amounts defined by routine testing in order to obtain optimal efficacy while minimizing any potential toxicity.

In addition to methods of achieving targeted cell death, methods of studying splicing mechanisms are also provided for through the use of the alternative splicing constructs described herein. The present invention includes methods of testing for pre-mRNA splicing in a cell comprising:
 a. providing the cell comprising an alternative splicing construct, wherein the splicing construct comprises a promoter operably linked to, in 5' to 3' order, a CD44 exon 5 or a fragment thereof, an intervening nucleic acid sequence containing one or more stop codons, a variable CD44 exon or a fragment thereof, and a nucleic acid sequence encoding an indicator protein;
 b. transcribing a pre-mRNA sequence from the splicing construct; and
 c. testing for splicing, wherein expression of the indicator protein at a level above a control expression level indicates splicing.

Also included are methods of determining the effect of a compound on pre-mRNA splicing wherein the compound is administered to the cell prior to step b. above.

In preferred embodiments of testing for pre-mRNA splicing, the indicator protein is a fluorescent protein. The alternative splicing constructs of the present invention that contain a fluorescent reporter sequence provide accurate and quantifiable evidence of splicing events since the fluorescent protein is only expressed upon the splicing of the construct. These methods and constructs can be used to identify splicing activators, inhibitors, and the like. Fluorescence can be detected by any means known to those of skill in the art including, but not limited to, flow cytometry, fluorescent microscopy, fluorescent plate reader, fluorescent spectroscopy, and fluorescence tomography (as used with whole body imaging).

In some embodiments, the alternative splicing construct used in the testing methods is a CD44v6 alternative splicing construct comprising a CD44 exon 5, a CD44 intron 9-10 nucleotide sequence, a CD44 exon 10 sequence, and a fluorescent protein encoding sequence. In one embodiment, the CD44 exon 5 nucleotide sequence comprises SEQ ID NO:1, the CD44 intron 9-10 nucleotide sequence comprises SEQ ID NO:2 or SEQ ID NO:3, the CD44 exon 10 nucleotide sequence comprises SEQ ID NO:4, and a fluorescent protein encoding sequence. In other embodiments, the alternative splicing construct used in the testing methods is a CD44v8 alternative splicing construct comprising a CD44 exon 5, a CD44 intron 11-12 nucleotide sequence, a CD44 exon 12 sequence, and a fluorescent protein encoding sequence. In one embodiment, the CD44 exon 5 nucleotide sequence comprises SEQ ID NO:1, the CD44 intron 11-12 nucleotide sequence comprises SEQ ID NO:6, and the CD44 exon 12 nucleotide sequence comprises SEQ ID NO:5.

The testing methods also include the use of an alternative splicing construct comprising a CD44 exon 5 nucleotide sequence that has approximately 99%, 98%, 97%, 96%, 95%, 94%, 93%, 92%, 91%, 90%, 85%, 80%, 75%, 70%, 60%, 50%, or 40% sequence homology with SEQ ID NO:1, a CD44 intron 9-10 nucleotide sequence that has approximately 99%, 98%, 97%, 96%, 95%, 94%, 93%, 92%, 91%, 90%, 85%, 80%, 75%, 70%, 60%, 50%, or 40% sequence homology with SEQ ID NO:2 or SEQ ID NO:3, and a CD44 exon 10 nucleotide sequence that has approximately 99%, 98%, 97%, 96%, 95%, 94%, 93%, 92%, 91%, 90%, 85%, 80%, 75%, 70%, 60%, 50%, or 40% sequence homology with SEQ ID NO:4.

The testing methods further include the use of an alternative splicing construct comprising a CD44 exon 5 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:1, the CD44 intron 11-12 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:6, and the CD44 exon 12 nucleotide sequence has approximately 99%, 98%, 97%, 96%, 95%, 94%, 93%, 92%, 91%, 90%, 85%, 80%, 75%, 70%, 60%, 50%, or 40% sequence homology with SEQ ID NO:5.

It should be understood that the alternative splicing construct used in the methods of the present invention can contain any portion of a CD44 exon 5 nucleotide sequence that contains a first splice site recognition sequence. In one embodiment, an alternative splicing construct used in the testing methods comprises a 3' fragment of SEQ ID NO:1. The 3' fragment can contain 50%, 40%, 30%, 20%, 10%, 5%, 4%, 3%, 2% or 1% of the 3' half of SEQ ID NO: 1. In some embodiments, the alternative splicing construct comprises between 5-10, 5-15, 5-20 or 5-30 of the 3' nucleotides of SEQ ID NO:1.

It should be further understood that an alternative splicing construct administered according to the methods of the present invention can contain any portion of a CD44 exon 10, CD44 exon 12, CD44 intron 9-10, and/or CD44 intron 11-12 nucleotide sequence that contains a second splice site recognition sequence. In one embodiment, the alternative splicing construct is used in the testing methods, which construct comprises a 3' fragment of SEQ ID NO:2, SEQ ID NO:3, or SEQ ID NO:6. The 3' fragment can contain 50%, 40%, 30%, 20%, 10%, 5%, 4%, 3%, 2%, 1%, 0.5% or 0.25% of the 3' half of SEQ ID NO:2, SEQ ID NO:3, or SEQ ID NO:6. In some embodiments, the alternative splicing construct comprises between 5-10, 5-15, 5-20, or 5-30 of the 3' nucleotides of SEQ ID NO:2, SEQ ID NO:3, or SEQ ID NO:6. In another embodiment, the alternative splicing construct that is used in the testing methods comprises a 5' fragment of SEQ ID NO:4 or SEQ ID NO:5. The 5' fragment can contain 50%, 40%, 30%, 20%, 10%, 5%, 4%, 3%, 2% or 1% of the 5' half of SEQ ID NO:4 or SEQ ID NO:5. In some embodiments, the alternative splicing construct comprises between 5-10, 5-15, 5-20, or 5-30 of the 5' nucleotides of SEQ ID NO:4 or SEQ ID NO:5.

The compositions provided for detecting pre-mRNA splicing and studying splicing generally include the alternative splicing constructs described herein and cells comprising the alternative splicing constructs. The cell can be any cell in which splicing occurs. In a preferred embodiment, the cell is an MCF-7 cell (Michigan Cancer Foundation-7, breast cancer cell line). However, additional cell lines that may be used in the compositions and methods for detecting pre-mRNA splicing include ASML (rat pancreatic adenocarcinoma), A431 (SCC), UT-SCC12, SCC25, UM-SCC11B (HNSCC), PANC-1 (pancreatic cancer), MW35, SBcl2, WM793, WM278, WM9, WM164, 4511u, 12051u (human melanoma), MDA468 (human breast cancer), HepG2 (human hepatoma), RPMI8226 (multiple myeloma human), L9981 (non-small cell lung cancer human), HeLa (human cervical cancer), HT29 (human colon adenocarcinoma), RAW264.7 (mouse leukemia), B16F10 (mouse melanoma), A375 (human melanoma), NK-92 (human NK cell), SKBR-3 (human breast cancer), MDA-MB-468 (human breast cancer), K562 (human myelogenous leukemia), and any cell line that is created based upon a CD44v6 expressing cell described in Heider et. Al., Cancer Immonol. Immunother. 53:567-579 (2004). In some embodiments, the alternative splicing constructs are stably integrated into the genome of the cell. The compositions provided for detecting pre-mRNA splicing and studying splicing generally also include components designed for or used in high-throughput based assays, including, but not limited to, multi-well plates and reagents that facilitate detection of an indicator protein.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

All publications, patents and patent applications cited herein are hereby incorporated by reference in their entirety for all purposes.

EXAMPLES

Example 1

Construction of the GFP-Containing Splice Vector (pDD835)

The splice vector was constructed in three cloning steps. The plasmid pCMV6-Entry (available from Origen Technologies, Ltd., Rockville, Md.) was cut with SgfI and HindIII, then ligated to the 140 bp PCR of CD44 Exon 5 amplified with high-fidelity polymerase from MCF-7 genomic DNA with the primers E5SgfFor (5'-AAAA GCGATCGCATGACTATTGTTAACCGTGATGG-3') and NewE5HindRev (5'-TTGCAAGCTTTGGTAGCAGGG ATTCTGTC-3') (restriction sites underlined). This plasmid was then cut with HindIII and MluI and ligated to the 2853 bp PCR of CD44 Intron 9-10 and Exon 10 amplified from MCF-7 genomic CD44 DNA with the primers I10HindFor (5'-ACAAAAGCTTGTAAGCAAGATGG-3') and E10MluRev (5'-AAAAACGCGTACCAGCT GTCCCTG-3'), creating pDD826. Finally, pDD826 was cut with MluI and XhoI and ligated to the 720 bp PCR of eGFP from pcDNA3-eGFP with the primers YFPMluFor (5'-CGCC ACGCGTCAGAAGAACGGCATC-3') and YFPXhoRev (5'-AAAACTCGAGTTACTTGTACAGCTCGTC-3'). This resulted in the final fluorescent construct, pDD835. The GFP protein retains its native stop codon in this plasmid.

Example 2

Construction of the Toxin-Containing Splice Vector (pDD834)

The plasmid pDD826 was cut with MluI and NotI and ligated to the 409 bp PCR of the toxin vapC-1 from pDD686, a construct that contains the vapBC-1 operon from NTHi strain R2866 with a C-terminal polyhistidine epitope tag fused to vapC-1, using the primers C1MluFor (5'-GAGAACGCGTATGATTTATATGTTAG-3') and C1PetNotRev (5'-TTAAGCGGCCGCTTTGTTAGCAGCC-3'). This resulted in the VapC-1 toxin-containing plasmid pDD834.

Example 3

Transfection of Breast Cancer Cells Lines with Splice Vectors

MCF-7 and SKBR-3 breast cancer cell lines were transfected with 1 or 2 µg of various splice vectors (pDD835 or pDD834) or control vectors using the Nucleofector II device (Lonza, Basil Switzerland) using program P20 specifically designed for transfection of breast cancer cell lines. Transfections were performed following manufacturer's protocol. Following transfection, the cells were cultured in 6 well plates containing RPMI 1640 supplemented with 10% FBS for 24 to 48 hours.

Example 4

Detection of Properly Spliced mRNA by RT-PCR

To ensure that each exon was present and in the proper reading frame, RNA was isolated from transfected breast cancer cell lines and reverse transcribed into cDNA. The cDNA of cells transfected with the GFP-containing construct (pDD835) was amplified by PCR with the primers pCMVfor (5'-TTCGTCGACTGGATCCG-3') and c-MycRev (5'-CAGATCCTCTTCTGAG-3'). The cDNA of cells transfected with the vapC-1 containing vector (pDD834) was amplified by PCR with the primers pCMVfor (5'-TTCGTCGACTGGATCCG-3') and c-MycRev (5'-CAGATCCTCTTCTGAG-3'). The amplicons from the vector transfected cells were subjected to DNA sequencing to ensure that each exon was present and in the proper reading frame.

Example 5

Flow Cytometric Detection of GFP Expressing Cells

To determine whether the constructs were correctly spliced in-frame as to produce a mRNA that was translated into a functional protein, the breast cancer cells transfected with the GFP-containing splice vector (pDD835) were analyzed by flow cytometric analysis. More specifically, 24 and 48 hours following transfection the cells were harvested, prepared into a single cell suspension and the levels of GFP expression (mean fluorescence intensity) was determined by flow cytometric analysis (FACSAria II, Becton Dickenson, San Jose, Calif.). As a control, breast cancer cells transfected with control vectors were also analyzed. Ten thousand cells were analyzed per sample.

Example 6

Confirmation of Alternative Splicing of Test Plasmid pDD826 in MCF-7 Cells

RT-PCR was performed and followed by DNA sequencing to determine the sequence of the MCF-7 CD44v6 cDNA, and subsequently constructed a test plasmid with Exon 5, the intron immediately preceding Exon 10, and Exon 10 (pDD826) amplified from MCF-7 DNA. Two μg of this plasmid was used to transfect MCF-7 cells, and RT-PCR followed by sequencing determined that the vector was alternatively spliced such that Exon 5 and Exon 10 were in frame (FIGS. 2A and 2B).

Example 7

Figure 4:
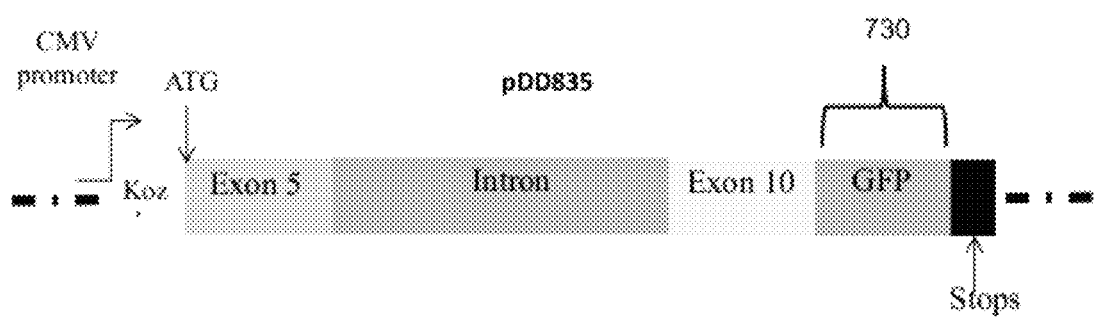
FIG. 4 is a schematic representation of an alternative splicing construct of the present invention (pDD835 plasmid) wherein a nucleic acid sequence encoding GFP is fused to CD44v6 Exon 10, wherein, "Koz" indicates a Kozak sequence.
Figure 5:
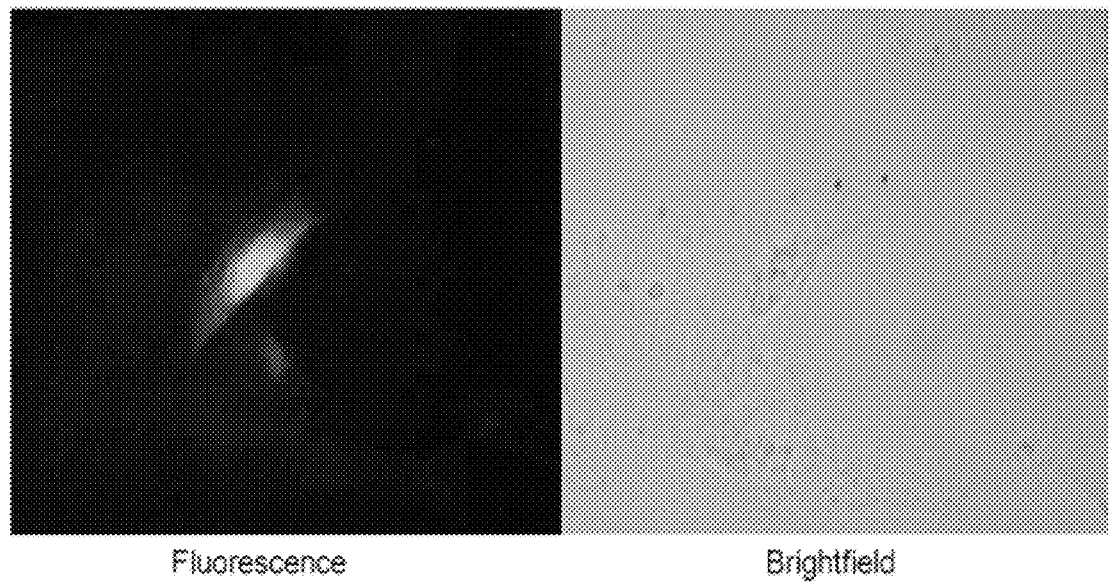
FIG. 5 shows the results of fluorescent microscopy which revealed that MCF-7 cells transfected with the pDD835 alternative splicing construct expressed high levels GFP (magnification of 1000×)
Figure 6:
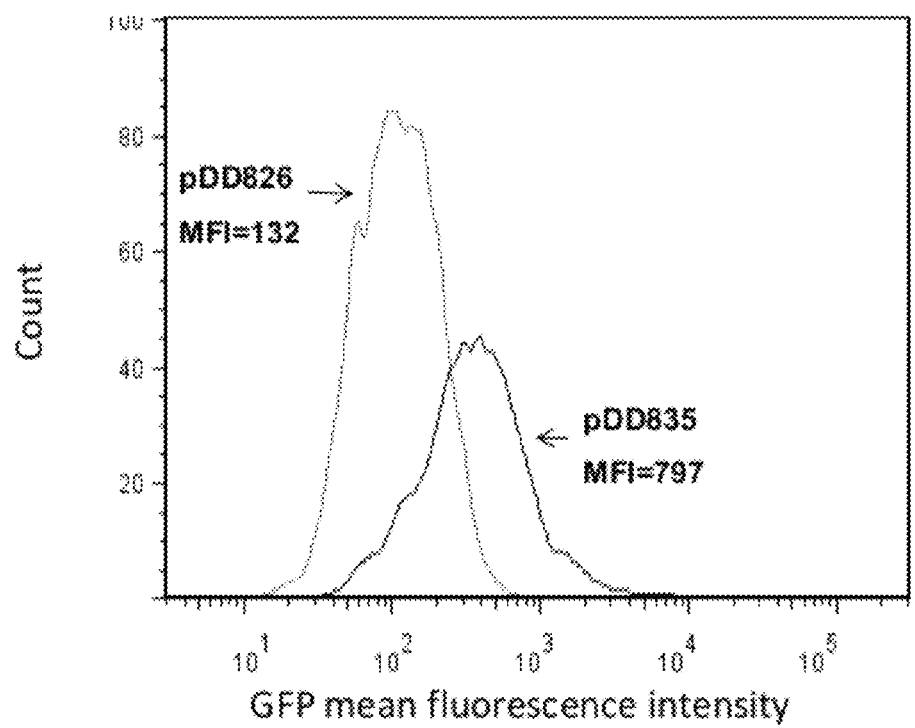
FIG. 6 is a graphic representation of flow cytometry results demonstrating GFP expression in MCF-7 cells transfected with the pDD835 alternative splicing construct.

Transfection of MCF-7 Breast Cancer Cells with GFP-Linked CD44v6 Splice Vector Leads to Production of GFP Based upon the above results, a plasmid with GFP fused to Exon 10, pDD835, was constructed (FIG. 4). This plasmid was used to transfect MCF-7 cells, and the cells were grown on a microscope slide (Cultureslide, BD Bioscience). At 48 hours following transfection, the cells were fixed and mounted. Fluorescent microscopy revealed that transfected MCF-7 cells expressed high GFP levels (FIG. 5, magnification of 1000×). Flow cytometry also showed increased GFP expression from the pDD835 construct as compared to the control pDD826 construct (FIG. 6).

Example 8

Expression of pDD835 is Restricted to CD44v6-Positive Cells

It is important that efficient splicing of the CD44v6-based splicing vector is only accomplished in CD44v6-positive cells and not in CD44v6-negative cells. To confirm this, MCF-7 (CD44v6-positive) and MDA-231 (CD44v6-negative) cells were transfected with 2 μg of the control vector (pDD826, no GFP) or the GFP-linked CD44v6 splicing vector pDD835, cultured for 48 hours, harvested and analyzed for GFP expression by flow cytometric analysis.

Figure 7A:
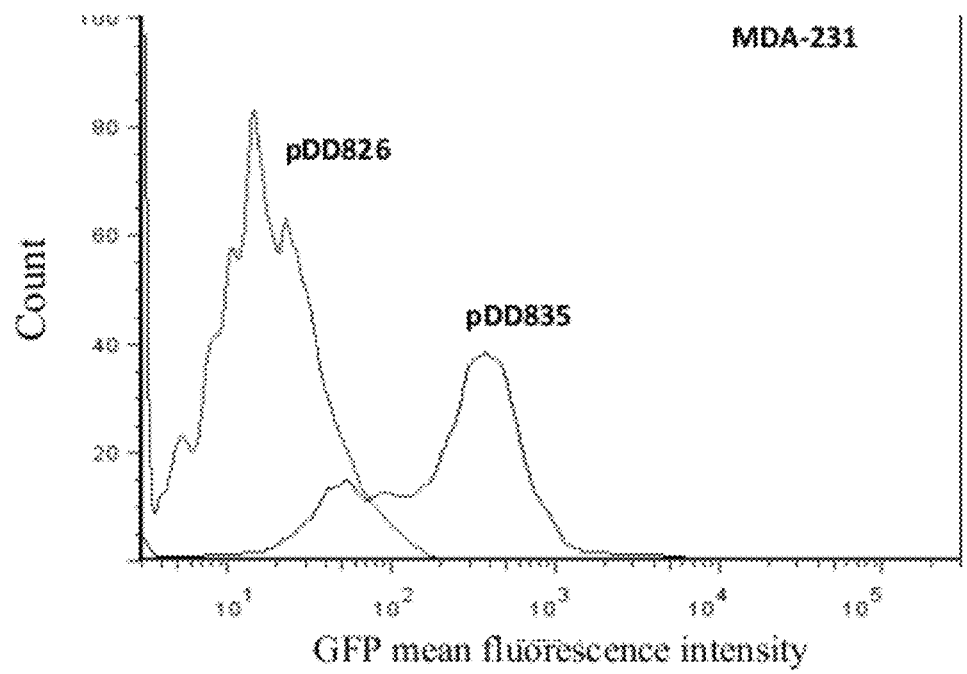
FIG. 7 is a graphic representation of flow cytometry results demonstrating that GFP expression from the pDD835 alternative splicing construct is restricted to CD44v6 positive cells.
Figure 7B:
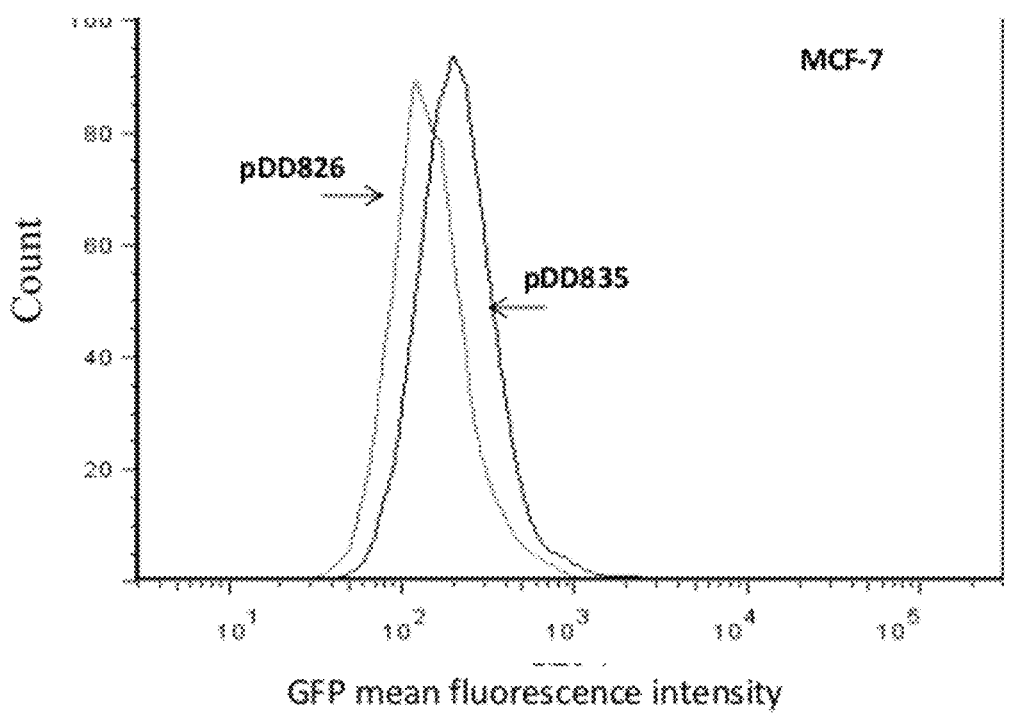

The results demonstrated that following transfection with pDD835, there was a significant increase in detectable GFP expression in the MCF-7 cells (FIG. 7A). In contrast, transfection of MDA-231 cells with the GFP-linked CD44v6 splice vector led to a minimal increase GFP expression (FIG. 7B). Transfection efficiencies, based on a separate transfection with the control pMaxGFP plasmid (Lonza) for MDA-231 and MCF-7, were 66% and 69%, respectively. Taken together, the results indicate that the CD44v6 splice vector-driven expression of proteins is optimal in cells that express CD44v6, indicating that expression vectors based on alternative splicing may be a novel tool for targeted cancer treatments.

Example 9

Effect of the Toxin-Linked CD44v6 Splice Vector pDD871 on MCF-7 Cells

In order to examine the potential therapeutic use of toxin-linked CD44v6 splice vectors in MCF-7 cells, a CD44v6 splice vector was developed in which the splice vector was linked to the catalytic portion of *P. aeruginosa* exotoxin A (PE). The toxin was designed to exclude any of the receptor binding domains of the protein, and therefore the truncated toxin could not bind to its native extracellular receptor. This minimizes any bystander killing resulting from the release of the toxin protein from dying cells.

Figure 8A:
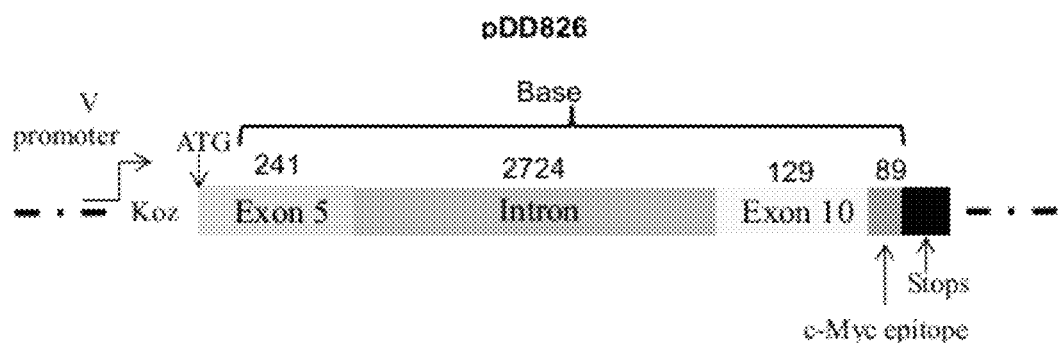
FIGS. 8A-8D contain schematic representations of alternative splicing constructs pDD826 and pDD871 (FIGS. 8A and 8B) and photographs demonstrating that expression of the pDD871 construct containing hPE24 results in reduced cell viability/adherence (FIGS. 8C and 8D), wherein "Koz" indicates a Kozak sequence.
Figure 8B:
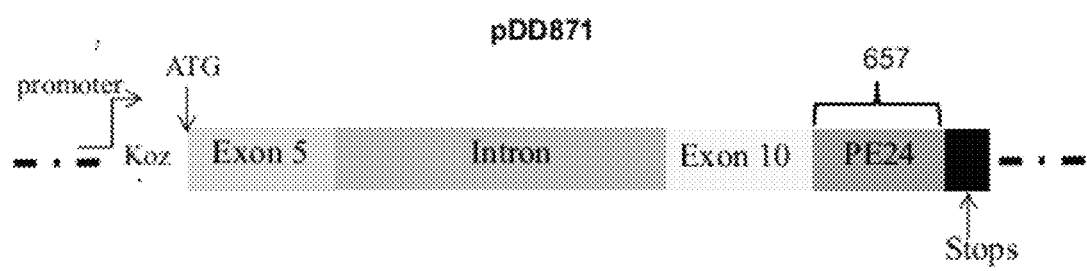

This vector was produced by replacing the GFP gene fusion in pDD835 with the catalytic portion of *P. aeruginosa* exotoxin A, termed PE24 (since the cytosolic toxin moiety is 24 kilodaltons), thus creating pDD871 (FIG. 8B). This was accomplished by amplifying the portion of the exotoxin A gene that corresponded to the final 219 amino acids of the toxin (amino acids 395 to 613) from *P. aeruginosa* PA01 genomic DNA using high fidelity polymerase with primers containing engineered MluI and EcoRV sites. This fragment was then cloned in-frame with Exon 10, such that a fusion protein consisting of the 5-10 protein and PE24 was expressed in CD44v6 expressing cells. Proper construction of pDD871 was confirmed by DNA sequencing and biologic activity was tested in MCF-7 breast cancer cells.

Figure 8C:
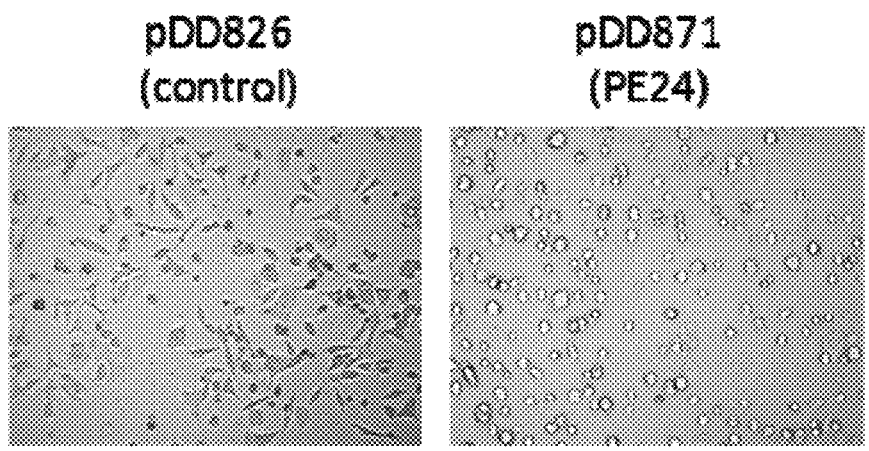
Figure 8D:
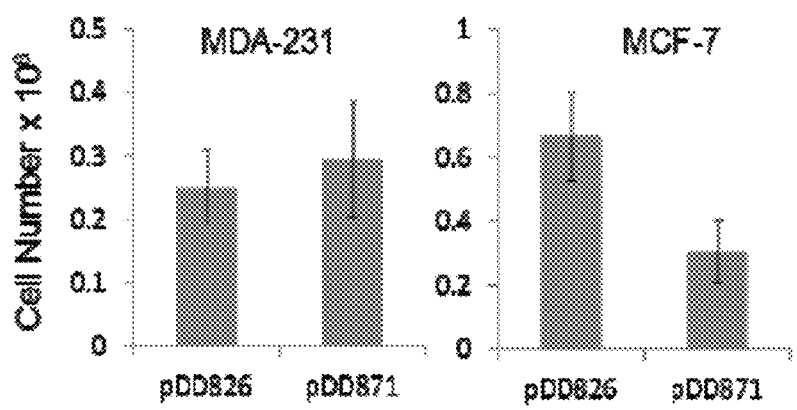

MCF-7 and MDA-231 cells were transfected with 2 μg control (pDD826) or the PE24-linked CD44v6 splice vector (pDD871). PE acts by inhibiting protein synthesis through ADP-ribosylation of EF-2 (Iglewski, B. H. and Kabat, Proc. Nat. Acad. Sci. USA 72:2284-8 (1975); Iglewski, B. H. et al., Infect. Immun. 15:138-44 (1977)). An early sign of reduced protein synthesis in adherent cells is their inability to maintain adherence to cell culture plates. Therefore, the activity of pDD871 was assessed 24 hours after transfection by quantifying the number of adherent/viable MCF-7 and MDA-231 cells. The results demonstrated that, following transfection with control vector, MCF-7 remained viable and was able to bind to tissue culture plates. In contrast, transfection of MCF-7 cells with the PE24-linked splice vector pDD871 led to a significant reduction in the number of viable/adherent cells. The effect of pDD871 is shown in a representative set of pictures illustrating the effect on MCF-7 morphology (FIG. 8C) and following quantification of adherent/viable cell number (FIG. 8D). Transfection of MDA-231 cells with pDD871 did not lead to significant changes in the number of adherent/viable cells. Together, these results indicate that transfection with the initial toxin-linked CD44v6 splice vector (pDD871) leads to significant biological activity that is restricted to CD44v6-positive cells.

Example 10

Figure 9A:
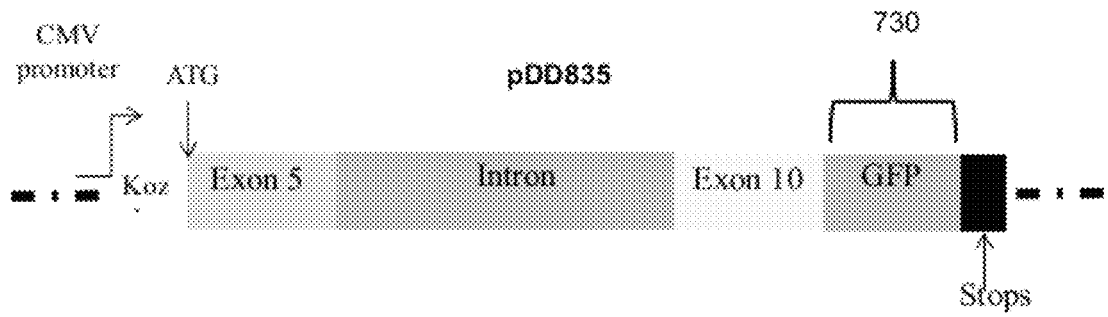
FIGS. 9A-9C contain schematic representations of alternative splicing constructs pDD835 and pDD865 (FIGS. 9A and 9B) and a graphic representation of results demonstrating that the reduction of intron size can increase GFP expression (FIG. 9C), wherein "Koz" indicates a Kozak sequence.
Figure 9B:
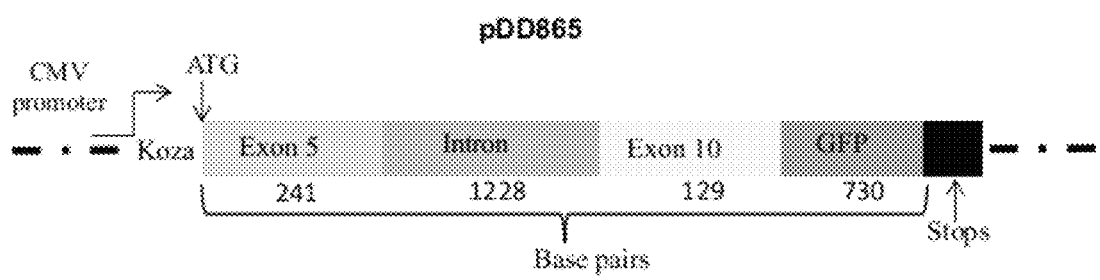
Figure 9C:
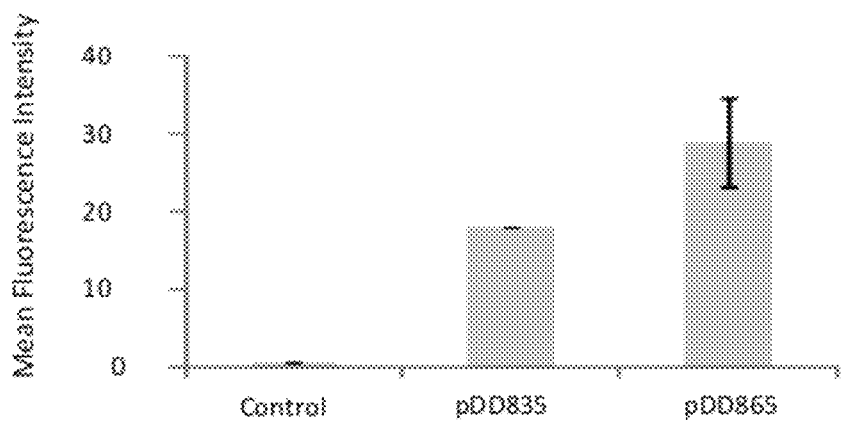

Reducing the Size of the Intron Results in More Efficient Transfection and Expression In reducing the size of the intron, the GFP-linked splice vector pDD835 was used as the parent plasmid and 1,495 bp was deleted from the original 2,724 bp intron. The resulting vector was gel-purified and religated, creating pDD865. This was accomplished by digesting pDD835 with the restriction enzyme XmnI, as there are two XmnI sites separated by 1,495 bp in the intron, but not anywhere else in the vector. Expression of GFP was then tested in MCF-7 cells transfected with the control vector (pDD826, no GFP) or pDD835 (FIG. 9A) or pDD865 (FIG. 9B). FIG. 9C illustrates that the expression of GFP was significantly enhanced in MCF-7 cells with pDD865, the GFP-linked vector with the smaller intron. This finding suggests that determining the optimal size for transfection and/or expression of linked proteins in the splice vectors will result in a more efficient system for therapeutic use.

Example 11

Development of Additional CD44 Splicing Vectors Such as CD44v8

Figure 10:
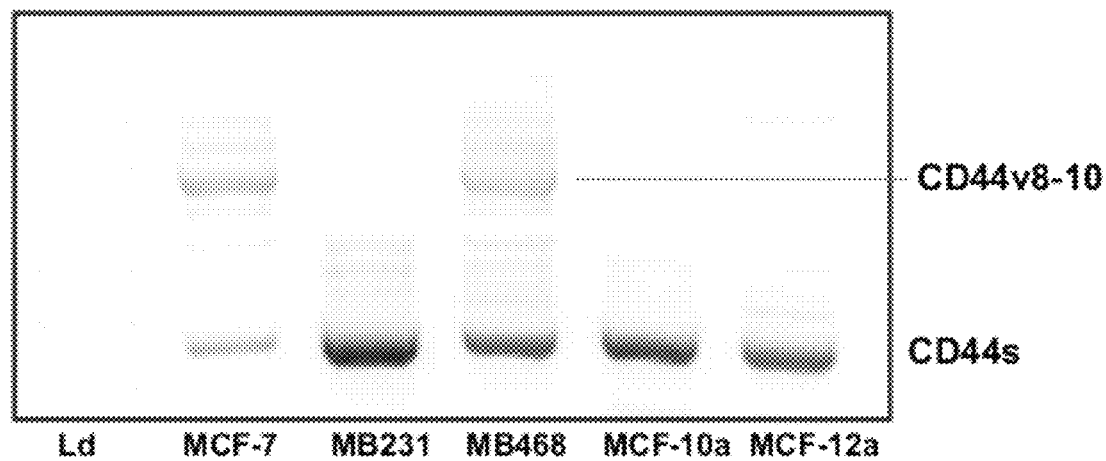
FIG. 10 is a southern blot analysis which demonstrates unique CD44 isoforms expressed by various breast cancer cell lines.
Figure 11A:
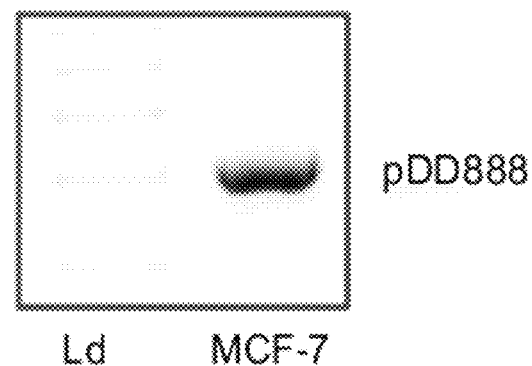

The expression of CD44 isoforms in five breast cancer cell lines was determined by RT-PCR. Using primers specific for CD44s (Exon 5 and Exon 15) a number of bands were identified. The results are shown in FIG. 10. The lower band in FIG. 10 corresponds to CD44s and was expressed by all cell lines tested. In addition, a unique band was visualized in the highly metastatic MCF-7 and MB-468 cell lines. This band was further characterized by sequencing and was determined to be the CD44 isoform CD44v8-10. After identifying the unique expression of CD44v8-10 in the MCF-7 and MB-468 cell lines, a splicing vector was designed that contained CD44 Exon 5 linked to the upstream intron associated with CD44 Exon 12, also referred to herein as CD44 Intron 11-12 (pDD888). Next, pDD888 was transfected into MCF-7 breast cancer cells using the Nucleofector transfection device. Expression of the splice vector mRNA product was determined 24 hours later by RT-PCR using primers that annealed inside Exon 5 and to a c-Myc tag in the vector sequence downstream of Exon 12 (FIG. 11A). The fragment was also subjected to DNA sequencing, which confirmed the proper splicing of the pre-mRNA from pDD888 (FIG. 11B).

Example 12

Expansion to Use in K562 Leukemia Cells

The expression of CD44v6 and CD44v8 was characterized in the K562 and Jurkat leukemia cell lines. RNA was isolated from K562 and Jurkat cells and the expression of CD44 variants containing the v6 and v8 exons was determined by RT-PCR (FIG. 12A). The results showed that K562 cells express CD44 isoforms containing the v6 and v8 variant exons. In contrast, Jurkat cells were negative for the expression of CD44v6 and CD44v8.

Since the K562 leukemia cells naturally expressed the v6 and v8 exons, it was then determined if these cells would also express the CD44v6 and CD44v8 splice vectors. K562 cells were transfected with either the CD44v6 splice vector (pDD826) or the CD44v8 splice vector (pDD888). RNA was isolated from the transfected cells 24 hours later and the expression of the splice vector was determined by RT-PCR. PCR was performed using a CD44 Exon 5-specific forward primer combined with a c-Myc-specific reverse primer with an expected product size of 420 bp and 183 bp, respectively. The results demonstrated that the splice vector transfected K562 cells produced products of the expected sizes (FIG. 12B).

Next, it was determined whether transfection of K562 leukemia cells with one or both of the GFP-linked CD44 splice vectors would lead to production of detectable levels of functional fluorescent protein. Linking GFP to the splice vector would allow for easy detection of protein resulting from proper splicing of the vector and subsequent translation of the spliced pre-mRNA. To this end, K562 cells were transfected with 2 µg of control (pDD826) or the GFP-linked CD44v6 splice vector (pDD835) using the Amaxa Nucleofector. In addition, K562 cells were transfected with 2 µg of control (pDD888) or the GFP-linked CD44v8 splice vector (pDD899). The cells were plated in 6 well plates, harvested 48 hours later, and assessed for GFP expression using flow cytometry.

Figure 13:
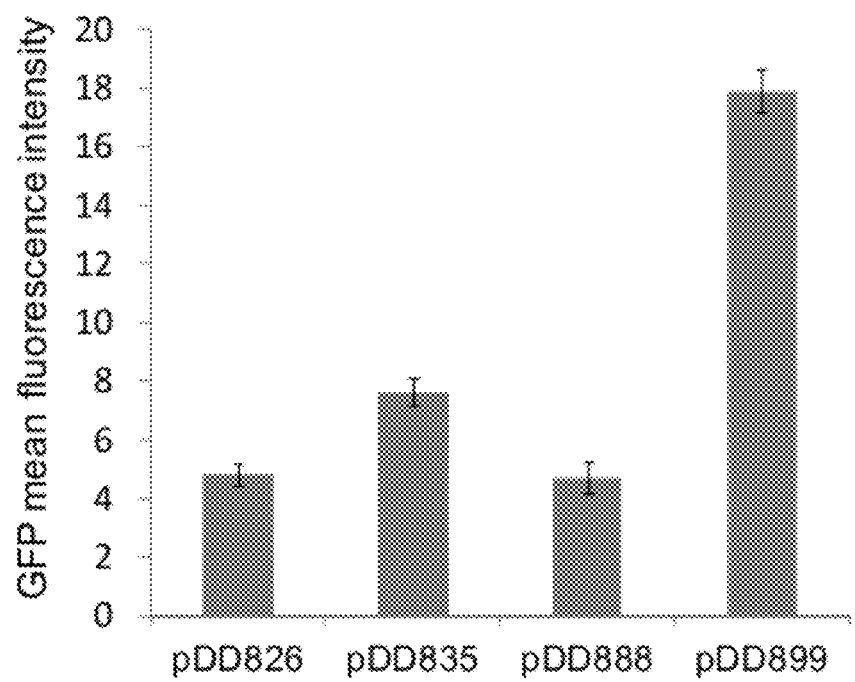
FIG. 13 is a graphic representation of data showing GFP expression following transfection of K562 cells with various alternative splicing constructs (pDD826, pDD835, pDD888 and pDD899)

The results demonstrated that following transfection with the GFP-linked CD44v6 splice vector or the GFP-linked CD44v8 splice vector, K562 leukemia cells were able to properly splice the pre-mRNA and produce detectable levels of GFP (FIG. 13). Taken with the findings of Example 11, these results demonstrate that the concepts described herein allows for the making of additional splicing vectors related to other CD44 isoforms that are now known or later found.

Example 13

Figure 14A:
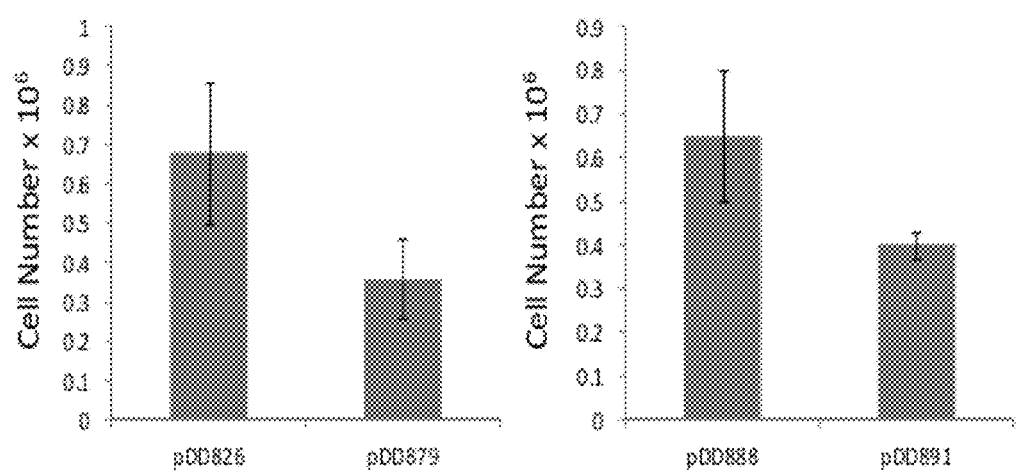
FIGS. 14A-14B provide a graphic representation of data showing a reduction in viability of K562 cells after transfection with alternative splicing constructs pDD871 and pDD891 which encode hPE24 (FIG. 14A trypan blue and FIG. 14B Annexin V/PI)
Figure 14B:
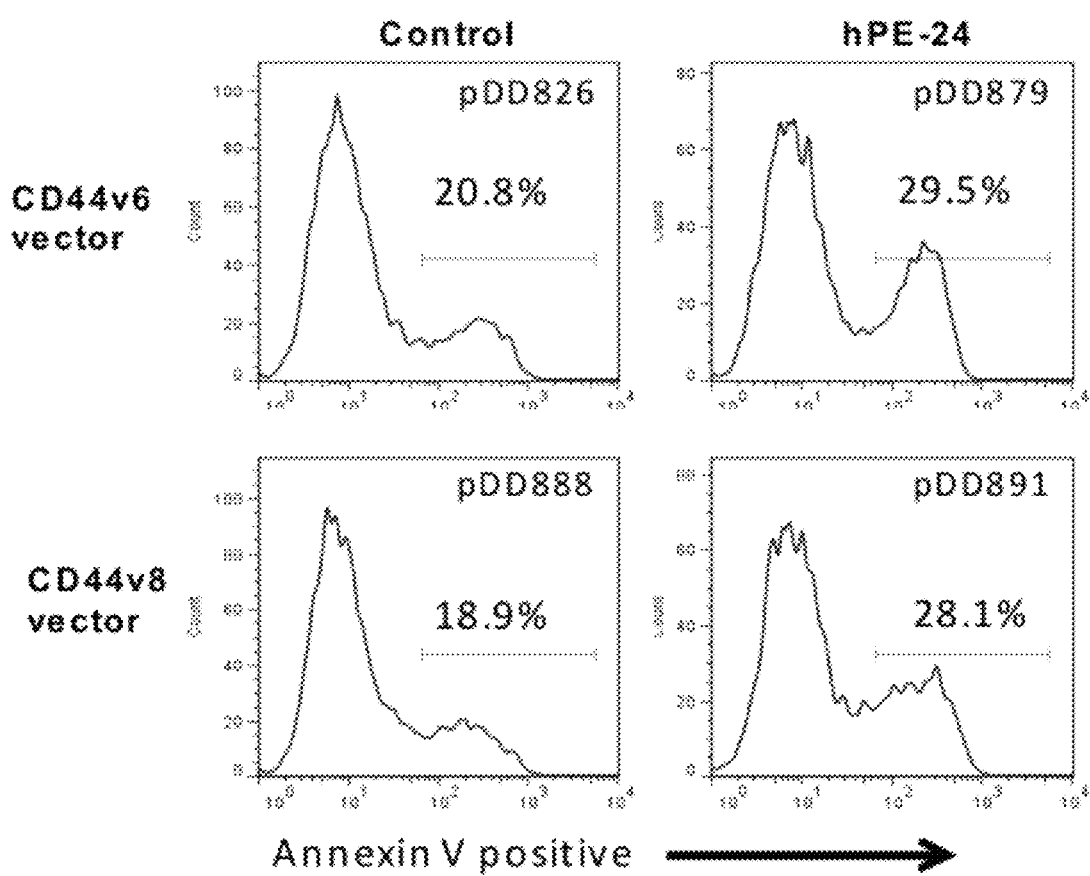

Effect of the Toxin-Linked CD44v6 (pDD879) and Toxin-Linked CD44v8 Splice Vector (pDD891) on K562 Leukemia Cells K562 cells were transfected with 2 µg control (pDD826 or pDD888) or the hPE24-linked CD44 splice vectors (pDD879 or pDD891). hPE24 is a 24 kDa fragment of *P. aeruginosa* exotoxin A as described in Example 9 that was further modified for human codon usage. hPE24 was fused to Exon 12 in pDD891, or Exon 10 in pDD879. PE acts by inhibiting protein synthesis through ADP-ribosylation of EF-2, leading to cell death by apoptosis. Therefore, the activity of pDD879 and pDD891 was assessed 48 hours after transfection by quantifying the number of viable K562 cells by trypan blue dye exclusion (FIG. 14A) followed by assaying for the induction of apoptosis using the Annexin V/PI assay (FIG. 14B).

The results demonstrated that, following transfection with either control splice vector, K562 cells remained viable. In contrast, transfection of K562 cells with either hPE24-linked splice vector led to a significant reduction in the number of viable cells and to a substantial increase in the number of apoptotic cells. Together, these results indicate that transfection with hPE24-linked CD44 splice vectors leads to considerable biological activity of the toxin, which in turn, results in cell death.

Example 14

Effect of the Toxin-Linked CD44v8 Splice Vector (pDD891) on Naïve Human PBMCs

Figure 15:
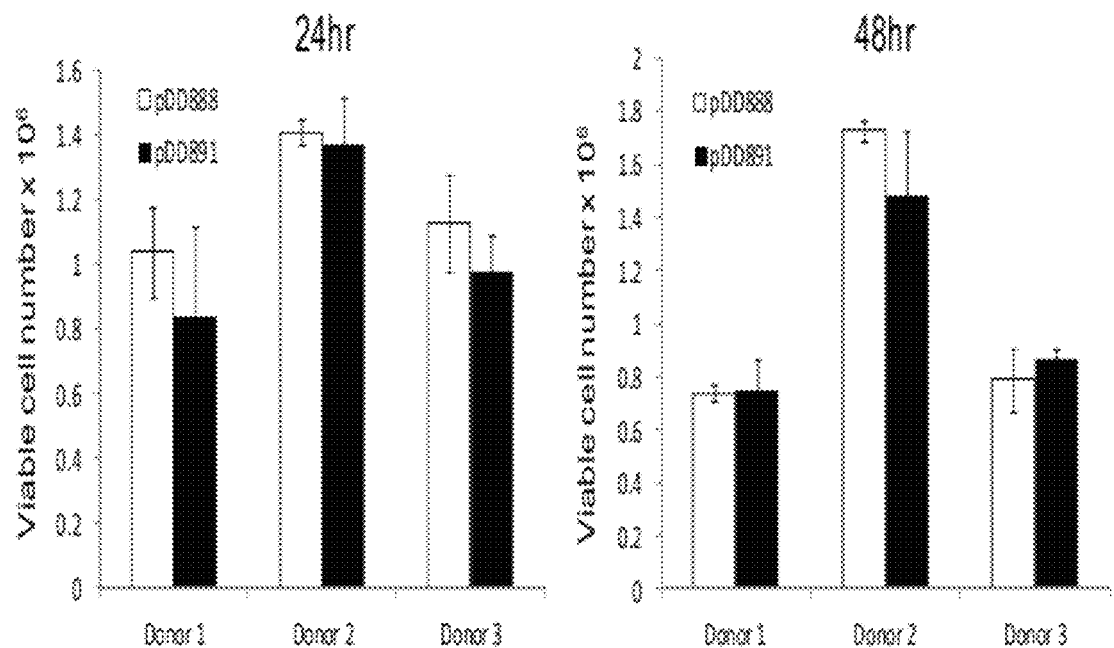
FIG. 15 is a graphic representation of data showing that human peripheral blood mononuclear cells are resistant to the effects of CD44v8 alternative splicing constructs.

Human PBMCs from three donors were transfected with 2 µg control (pDD888) or the hPE24-linked CD44v8 splice vector (pDD891). The effect of the splice vectors was assessed 24 and 48 hours after transfection by quantifying the number of viable PBMCs by trypan blue dye exclusion followed by assaying for the induction of apoptosis using the Annexin V/PI assay. The results demonstrated that, following transfection with the toxin-linked splice vector, there was no decrease in the number of viable PBMCs when compared to control vector transfected cells (FIG. 15). In addition, no significant increase in the level of apoptosis was observed in the PBMCs transfected with the toxin-linked splice vector, when compared to the levels of apoptosis seen in control vector-transfected cells (data not shown). Taken together, these results suggest that normal PBMCs are likely not sensitive to the effects of the toxin-linked splice vector.

Example 15

Assay for Testing the Effects of Compounds on Alternative Splicing

Figure 16A:
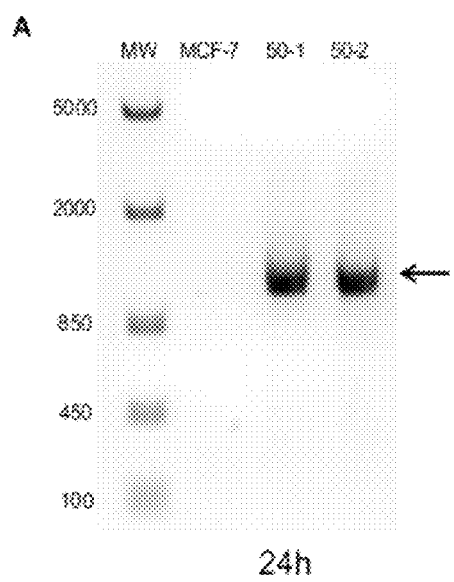
Figure 16B:
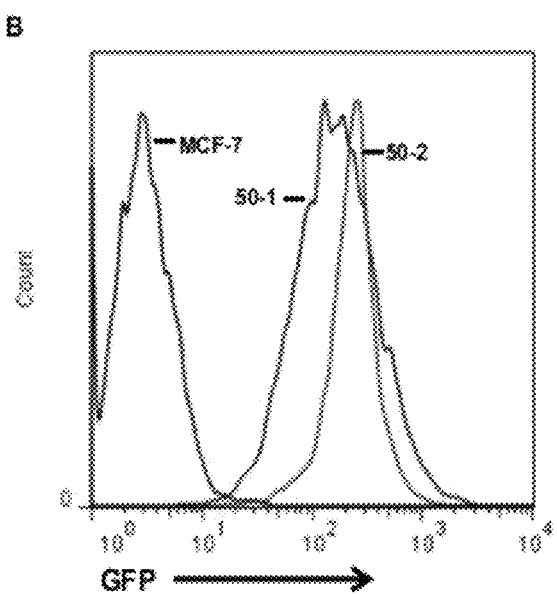
Figure 18:
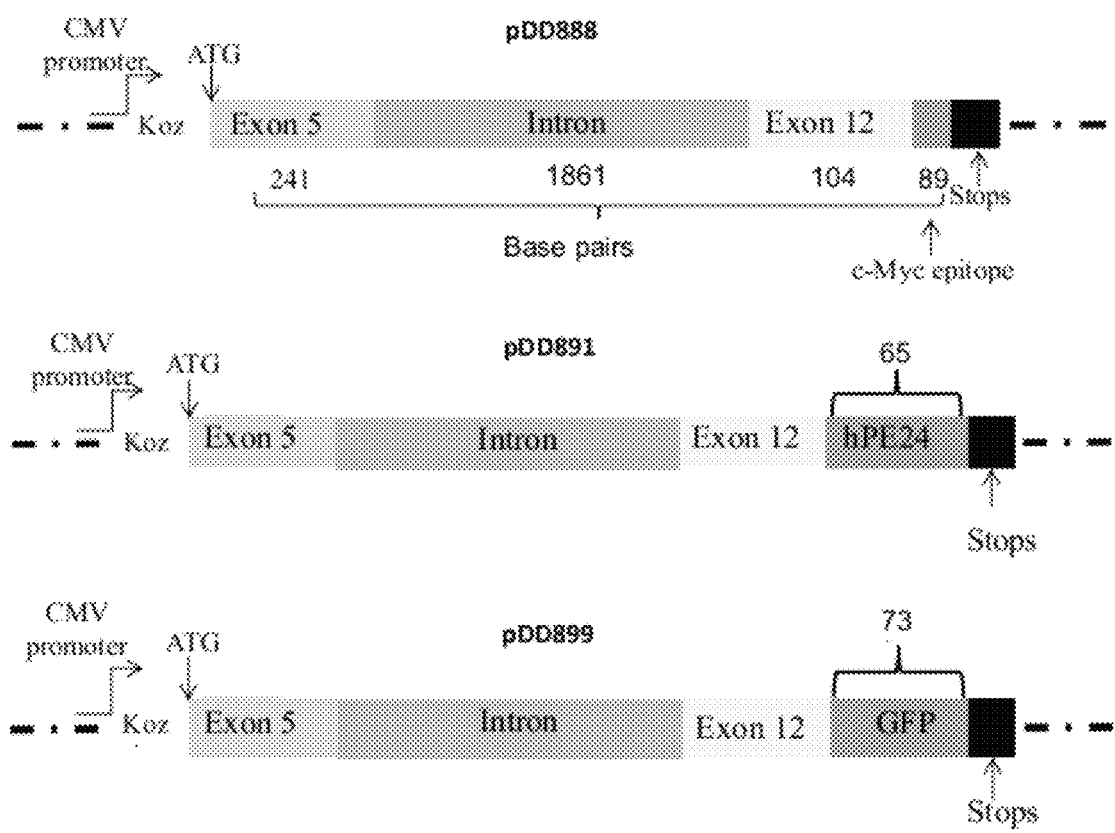
FIG. 18 contains schematic representations of several CD44v8 alternative splicing constructs, wherein "Koz" indicates a Kozak sequence.

One application of the splicing technology described herein is a plate-based high-throughput assay in which compounds that affect alternative splicing can be screened. In order to accomplish this, a cell line that stably expressed a splice vector construct linked to GFP was created using pLVX-Puro, a lentiviral vector. The insert from pDD835 (consisting of Exon 5, intron 9-10, Exon 10, GFP) was cloned into pLVX-Puro, creating pDD881. This plasmid was validated by sequencing. Using MCF-7 cells purchased directly from ATCC, two stable clones designated 50-1 and 50-2 were created. The only difference between these clones is that they were from two different transfections using the same GFP-linked insert. The clones were validated by RT-PCR using primers that annealed to Exon 5 and GFP (this resulted in a 1100 bp PCR product), followed by sequencing on both strands (FIG. 16A). GFP expression was determined by flow cytometry as well as fluorescence microscopy (FIGS. 16B and 16C).

Following construction of the MCF-7 cell lines that stably express and splice the GFP-linked CD44v6 splice vector, experiments were conducted to examine the utility of these cell lines in a plate-based splicing assay. To this end, various concentrations of the MCF-7 parent cells, 50-1, and 50-2 cells $(2 \times 10^4, 1 \times 10^4, 5 \times 10^3,$ and $2.5 \times 10^3)$ were cultured in 96-well flat bottomed fluorescence plates. The level of fluorescence was determined 24 hours later using a fluorescence plate reader. The results demonstrated significant and concentration-dependent levels of detectable GFP from both the 50-1 and 50-2 clones (FIG. 17).

What is claimed is:

1. An alternative splicing construct comprising a promoter operably linked to, in 5' to 3' order, (i) a CD44 exon 5 or 5' fragment thereof, wherein the 5' fragment comprises the 5' splice recognition site of CD44 exon 5, wherein the CD44 exon 5 consists of SEQ ID NO: 1, (ii) an intervening nucleic acid sequence containing one or more stop codons, (iii) a variable CD44 exon or 3' fragment thereof, wherein the 3' fragment comprises the 3' splice recognition site of the variable CD44 exon, and (iv) a nucleic acid sequence encoding a toxin protein or an indicator protein.

2. The alternative splicing construct of claim 1, wherein the variable CD44 exon is a CD44 exon 10 nucleotide sequence.

3. The alternative splicing construct of claim 2, wherein the CD44 exon 10 nucleotide sequence comprises SEQ ID NO:4.

4. The alternative splicing construct of claim 1, wherein the variable CD44 exon is a CD44 exon 12 nucleotide sequence.

5. The alternative splicing construct of claim 4, wherein the CD44 exon 12 nucleotide sequence comprises SEQ ID NO:5.

6. The alternative splicing construct of claim 1, wherein the intervening nucleic acid sequence comprises a CD44 intron sequence.

7. The alternative splicing construct of claim 6, wherein the CD44 intron sequence is a CD44 9-10 intron sequence comprising SEQ ID NO:2.

8. The alternative splicing construct of claim 6, wherein the CD44 intron sequence is a CD44 9-10 intron sequence comprising SEQ ID NO:3.

9. The alternative splicing construct of claim 6, wherein the CD44 intron sequence is a CD44 11-12 intron sequence comprising SEQ ID NO:6.

10. The alternative splicing construct of claim 1, wherein the indicator protein is a fluorescent protein.

11. The alternative splicing construct of claim 1, wherein the toxin protein is a *Pseudomonas aeruginosa* exotoxin A protein.

12. An alternative splicing construct comprising a promoter operably linked to, in 5' to 3' order, (i) a CD44 exon 5 or 5' fragment thereof, wherein the 5' fragment comprises the 5' splice recognition site of CD44 exon 5, (ii) an intervening nucleic acid sequence containing one or more stop codons, (iii) a variable CD44 exon or 3' fragment thereof, wherein the 3' fragment comprises the 3' splice recognition site of the variable CD44 exon and (iv) a nucleic acid sequence encoding a toxin protein or an indicator protein, wherein the toxin protein is a *Pseudomonas aeruginosa* exotoxin A protein comprising SEQ ID NO:7.

13. A cell comprising the alternative splicing construct of claim 1.

14. An in vitro method of testing for pre-mRNA splicing in a cell comprising:
   a) providing the cell that contains the alternative splicing construct of claim 1, wherein the splicing construct comprises a nucleic acid sequence encoding an indicator protein;
   b) transcribing a pre-mRNA sequence from the splicing construct; and
   c) testing for splicing, wherein expression of the indicator protein at a level above a control expression level indicates splicing.

15. The method of claim 14, further comprising administering a compound to the cell prior to step b.

16. The method of claim 14, wherein the cell is a cancer cell.

17. The method of claim 16, wherein the cancer cell is an MCF-7 cell having the alternative splicing construct stably integrated into the cell's genome.

18. The method of claim 14, wherein the variable CD44 exon is a CD44 exon 10 nucleotide sequence.

19. The method of claim 18, wherein the CD44 exon 10 nucleotide sequence comprises SEQ ID NO:4.

20. The method of claim 14, wherein the intervening nucleic acid sequence comprises a CD44 intron sequence.

21. The method of claim 20, wherein the CD44 intron sequence is a CD44 9-10 intron sequence comprising SEQ ID NO:2.

22. A cell comprising the alternative splicing construct of claim 12.

* * * * *